(12) United States Patent
Polchin et al.

(10) Patent No.: US 12,636,116 B2
(45) Date of Patent: May 26, 2026

(54) ROBOTIC SURGICAL NAVIGATION USING A PROPRIOCEPTIVE DIGITAL SURGICAL STEREOSCOPIC CAMERA SYSTEM

(71) Applicant: Degital Surgery Systems, Inc., Gioletta, CA (US)

(72) Inventors: George Charles Polchin, Santa Barbara, CA (US); Simon Raab, Santa Barbara, CA (US)

(73) Assignee: Digital Surgery Systems, Inc., Goleta, CA (US)

( * ) Notice: Subject to any disclaimer, the term of this patent is extended or adjusted under 35 U.S.C. 154(b) by 189 days.

(21) Appl. No.: 17/773,500

(22) PCT Filed: Nov. 2, 2020

(86) PCT No.: PCT/US2020/058488
§ 371 (c)(1),
(2) Date: Apr. 29, 2022

(87) PCT Pub. No.: WO2021/087433
PCT Pub. Date: May 6, 2021

(65) Prior Publication Data
US 2022/0401178 A1 Dec. 22, 2022

Related U.S. Application Data

(60) Provisional application No. 62/929,421, filed on Nov. 1, 2019.

(51) Int. Cl.
*A61B 34/20* (2016.01)
*A61B 34/37* (2016.01)
(Continued)

(52) U.S. Cl.
CPC ............ *A61B 90/361* (2016.02); *A61B 34/20* (2016.02); *A61B 34/37* (2016.02);
(Continued)

(58) Field of Classification Search
None
See application file for complete search history.

(56) References Cited

U.S. PATENT DOCUMENTS 10,555,775 B2 * 2/2020 Hoffman .................. A61B 1/04
10,917,543 B2 * 2/2021 Ramirez Luna ....... B25J 9/0009
(Continued)

FOREIGN PATENT DOCUMENTS

WO 2021/087433 A1 5/2021

OTHER PUBLICATIONS

Extended European Search Report, dated Oct. 27, 2023, for European Application No. 20883410.1.
(Continued)

*Primary Examiner* — Chikaodili E Anyikire
(74) *Attorney, Agent, or Firm* — K&L Gates LLP

(57) ABSTRACT

A robotic surgical navigation system is disclosed. An example system includes a stereoscopic camera and a robotic arm having an end-effector connected to the camera. The system also includes a navigation computer that determines a first transformation between the stereoscopic camera and a target surgical site, a second transformation between the end-effector and a robotic base of the robotic arm, and a third transformation between the robotic base and the target surgical site. The navigation computer calculates a fourth transformation using the first, second, and third transformations. The fourth transformation represents a transformation between the end-effector and the stereoscopic camera. The navigation computer uses the transformations to determine coordinates for a view vector of the stereoscopic camera that are in a coordinate system of the robotic arm, thereby enabling movement of the robotic arm based on commands provided by an operator in relation to the view vector of the camera.

20 Claims, 15 Drawing Sheets

100

(51) Int. Cl.

| | |
|---|---|
| *A61B 90/00* | (2016.01) |
| *A61B 34/00* | (2016.01) |
| *A61B 34/30* | (2016.01) |

(52) U.S. Cl.

CPC . *A61B 2034/2057* (2016.02); *A61B 2034/305* (2016.02); *A61B 2034/742* (2016.02); *A61B 2090/064* (2016.02); *A61B 2090/364* (2016.02)

(56) References Cited

U.S. PATENT DOCUMENTS

| | | | |
|---|---|---|---|
| 11,903,659 B2 * | 2/2024 | Blondel | A61B 8/4218 |
| 2011/0190790 A1 * | 8/2011 | Summerer | A61B 34/76 |
| | | | 606/130 |
| 2016/0035079 A1 * | 2/2016 | Tenney | G06T 7/80 |
| | | | 382/153 |
| 2018/0071032 A1 | 3/2018 | de Almeida Barreto | |
| 2019/0223964 A1 * | 7/2019 | Navkar | A61B 34/20 |
| 2019/0298277 A1 * | 10/2019 | Zhang | A61B 34/30 |
| 2019/0327394 A1 | 10/2019 | Ramirez Luna et al. | |

| | | | |
|---|---|---|---|
| 2022/0175471 A1 * | 6/2022 | Pickett | A61B 34/30 |
| 2022/0377217 A1 * | 11/2022 | Dehghani | G02B 23/2423 |
| 2022/0401178 A1 * | 12/2022 | Polchin | A61B 34/20 |

OTHER PUBLICATIONS

Rao R Madhusudhan et al., "Development of a Robot-mounted 3D Scanner and Multi-view Registration Techniques for Industrial Applications," Procedia Computer Science, vol. 133, Jan. 1, 2018 (Jan. 1, 2018), pp. 256-267.

Taylor Zachary, "Camera to Robotic Arm Calibration," File Exchange—MatLab Central, Published Dec. 10, 2014, Updated: Jun. 11, 2016.

Gurevich Pavel et al., "Design and Implementation of TeleAdvisor: a Projection-Based Augmented Reality System for Remote Collaboration," Computer Supporter Cooperative Work, Dordrecht, NL, vol. 24, No. 6, Sep. 10, 2015 Sep. 10, 2015), pp. 527-562.

International Search Report and Written Opinion, mailed Jan. 28, 2021, for International Application Serial No. PCT/US2020/058488 filed Nov. 2, 2020.

* cited by examiner

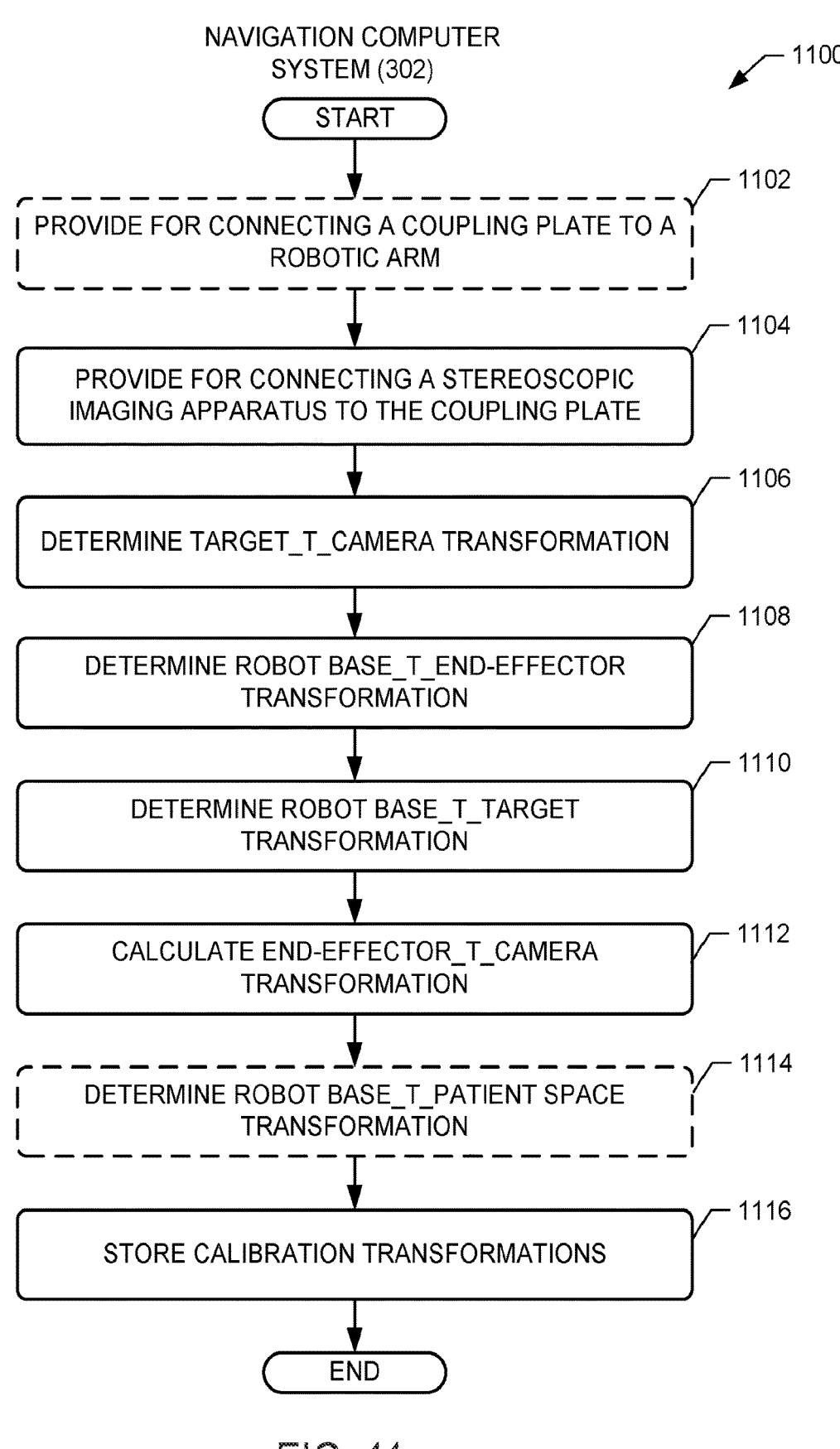

NAVIGATION COMPUTER
SYSTEM (302)

1100

START

PROVIDE FOR CONNECTING A COUPLING PLATE TO A ROBOTIC ARM — 1102

PROVIDE FOR CONNECTING A STEREOSCOPIC IMAGING APPARATUS TO THE COUPLING PLATE — 1104

DETERMINE TARGET_T_CAMERA TRANSFORMATION — 1106

DETERMINE ROBOT BASE_T_END-EFFECTOR TRANSFORMATION — 1108

DETERMINE ROBOT BASE_T_TARGET TRANSFORMATION — 1110

CALCULATE END-EFFECTOR_T_CAMERA TRANSFORMATION — 1112

DETERMINE ROBOT BASE_T_PATIENT SPACE TRANSFORMATION — 1114

STORE CALIBRATION TRANSFORMATIONS — 1116

END

FIG. 11

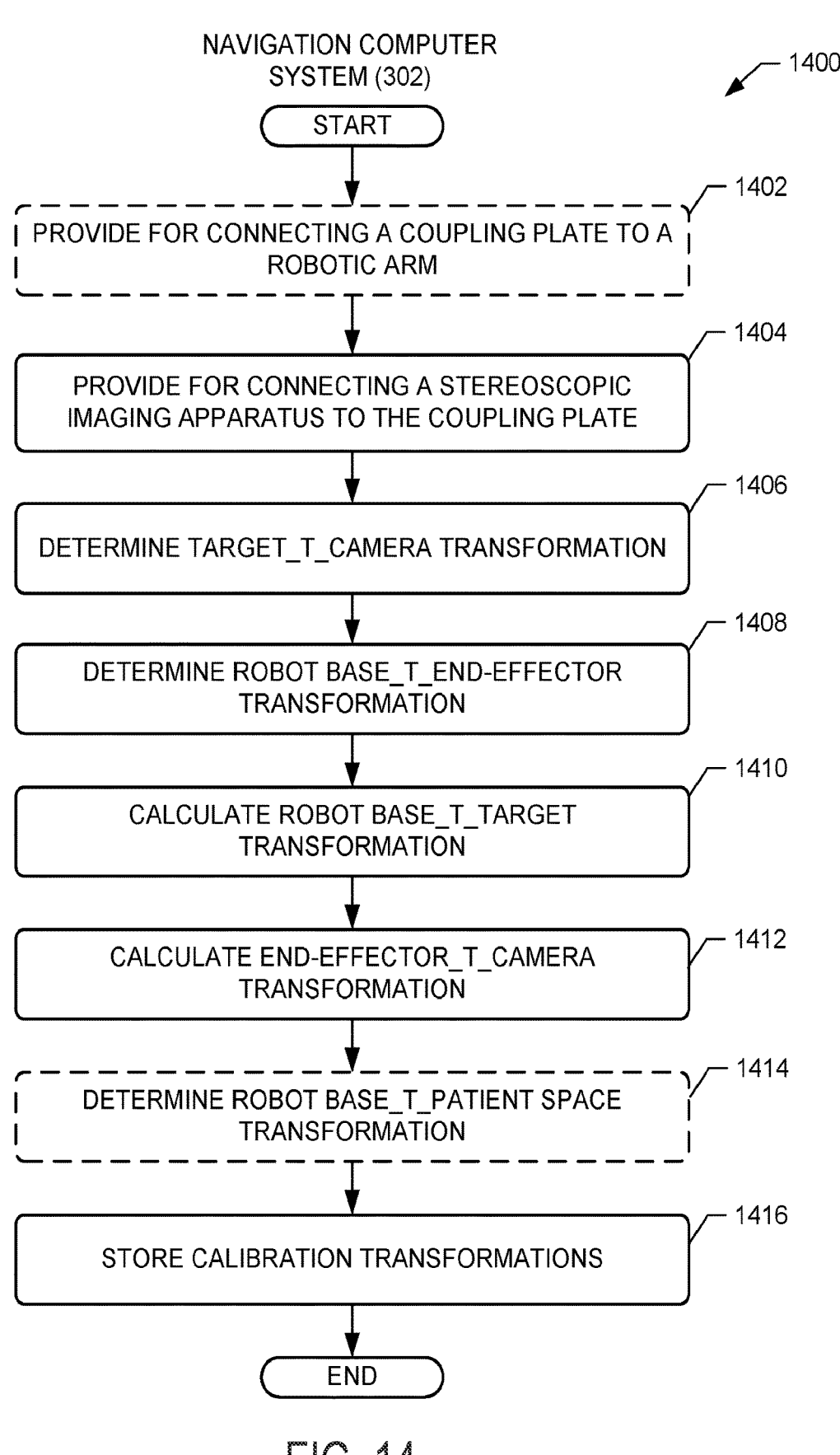

NAVIGATION COMPUTER
SYSTEM (302)

START

1402   PROVIDE FOR CONNECTING A COUPLING PLATE TO A ROBOTIC ARM

1404   PROVIDE FOR CONNECTING A STEREOSCOPIC IMAGING APPARATUS TO THE COUPLING PLATE

1406   DETERMINE TARGET_T_CAMERA TRANSFORMATION

1408   DETERMINE ROBOT BASE_T_END-EFFECTOR TRANSFORMATION

1410   CALCULATE ROBOT BASE_T_TARGET TRANSFORMATION

1412   CALCULATE END-EFFECTOR_T_CAMERA TRANSFORMATION

1414   DETERMINE ROBOT BASE_T_PATIENT SPACE TRANSFORMATION

1416   STORE CALIBRATION TRANSFORMATIONS

END

ROBOTIC SURGICAL NAVIGATION USING A PROPRIOCEPTIVE DIGITAL SURGICAL STEREOSCOPIC CAMERA SYSTEM

PRIORITY CLAIM

The present application is a national phase filing of International Application No. PCT/US2020/058488, filed Nov. 2, 2020, which claims priority to and the benefit of U.S. Provisional Application No. 62/929,421, filed Nov. 1, 2019. The entire contents of each application are incorporated herein by reference and relied upon.

TECHNICAL FIELD

The present invention relates to stereoscopic surgical cameras, and more specifically to a robotic surgical navigation system that uses pose information from a proprioceptive stereoscopic digital surgical camera system for controlling robotic arm movement.

BACKGROUND

A surgical imaging system typically includes a camera or a microscope mounted on a robotic arm. The imaging system also includes a computer system that controls the camera or microscope and positioning of the robotic arm. Oftentimes, the computer system includes a surgical navigation system that attempts to correlate or register a position of a live patient to a set of patient data, such as volumetric computed tomography ("CT") data, magnetic resonance imaging ("MM") data, preoperative images, and/or three-dimensional surgical guidance visualizations. The goal of these known navigation systems is to provide an operator with an approximate knowledge of where in the patient anatomy (which comprises a three-dimensional space) the operator is currently "looking" via the camera, microscope, or a probe. A location of a probe tip is a primary object of interest when a traditional probe is used. In the case of a camera or microscope, the location of camera or microscope's focal point is the primary object of interest.

In some instances, an orientation of a vector along which the traditional probe lies is also of interest for surgical navigation. In the case of a surgical camera or microscope, the vector is referred to as a view axis orientation or a view vector. The view axis orientation refers to a line of sight of the camera or microscope. Generally, when an operator uses a controller to move the surgical camera or microscope, they provide control inputs relative to their line of sight. For instance, if an operator wants to move a camera to the "right", the operator will select a right arrow control or move a joystick control or foot pedal to the "right". However, depending on the current pose of the camera or robotic arm holding the camera, a control input to move in a right direction may cause the camera to move "left", "up" or at an angle. This disjoint association between view angle and camera/robotic arm pose can cause operator frustration, especially while in the middle of an intricate surgical procedure.

Stereoscopic (also known as three-dimensional ("3D")) surgical microscopes have recently been replaced by digital stereoscopic cameras mounted on robotic arms. The known stereoscopic systems include an associated stereoscopic display, which eliminates the need for an operator to be physically coupled to microscope oculars. Instead, the operator can operate "heads up" by allowing the camera to be positioned as needed while always mounting a display screen in a physically neutral position. The operator only needs to view the surgical scene provided on the display screen, and no longer needs to look through oculars of a microscope, which can sometimes been positioned awkwardly and place strain on an operator's neck and back.

In some instances, a stereoscopic camera can be modeled as two monoscopic cameras. The view vector of a given monoscopic camera is defined as the view into the scene along a vector passing through the center of the display. The camera itself includes a specific orientation about that axis such that the "up" and "right" directions are known, which enable alignment of an operator's view to the scene. However, oftentimes the orientation of the robotic arm is not associated with the orientation of the camera. This means commands to move the robotic arm may not correspond to the surgical view shown by the camera. Further, a position and/or orientation of a coupling plate that connects the robotic arm to the camera may not be accounted for by a surgical navigation system, thereby further creating opportunities for misalignment between a view vector of the camera and the known pose of the robotic arm.

SUMMARY

A surgical navigation system is disclosed herein that creates an accurate correspondence between a view vector of a stereoscopic camera and a pose of a robotic arm. The example surgical navigation system identifies an unknown orientation and position (e.g., a pose) of an end-effector that is located between the stereoscopic camera and the robotic arm. Oftentimes, a coupling plate couples the camera to the robotic arm, where a position and orientation of the coupling plate is not known to the surgical navigation system. The surgical navigation system uses transformation matrixes between known poses of the robotic arm, the stereoscopic camera, and a target surgical site to determine the unknown orientation and position of the end-effector, including the coupling plate. Once the orientation and position of the end-effector is known, the surgical navigation system can determine an accurate correspondence between a view vector of the stereoscopic camera and a pose of the robotic system.

The surgical navigation system uses the accurate correspondence between a view vector of the stereoscopic camera and a pose of the robotic system for controlling movement of the robotic arm. For instance, an operator may be viewing on a display screen a live surgical image recorded by the stereoscopic camera. The operator uses a controller, joystick, or force sensors attached to the camera to enter a command to move "right" relative to the current view. However, given the orientation and position of the robotic arm, stereoscopic camera, and coupling plate, this "right" command is not simply translated into a command that causes the robotic arm to move to the right. Instead, the disclosed surgical navigation system uses the known correspondence between the view vector and the pose of the robotic system (including the robotic arm, camera, coupling plate, and surgical target) to command one more joints of the robotic arm to rotate in a specified manner, the end result of which causes the stereoscopic camera to move "right", as commanded by the operator.

As disclosed herein, the surgical navigation system determines a correspondence or correlation between a view vector of the stereoscopic camera and a pose of the robotic system using known and unknown transformations. The correspondence or correlation between the view vector of the stereoscopic camera and the pose of the robotic system may include an expression of the view vector of the stereoscopic camera in a coordinate system of the robotic system. The transformations provide a linkage between an orientation and position of a target to a robotic arm base and the stereoscopic camera. The transformations may include a first transformation between a pose (e.g., a position or orientation) of the robotic arm base and a pose the target surgical site, a second transformation between the pose the robotic arm base and a pose of the robotic arm end-effector, a third transformation between the pose of the robotic arm end-effector and a pose of the stereoscopic camera, and a fourth transformation between the pose of the stereoscopic camera and the target surgical site. The first transformation may be known or unknown to the surgical navigation system, while the third transformation is always unknown to the surgical navigation system. The second transformation is known by the surgical navigation system from joint sensor feedback (e.g., pose data) of the robotic arm. The fourth transformation is known by the surgical navigation system from intrinsic and/or extrinsic camera parameters. As described herein, the surgical navigation system use certain equations and/or matrix computations between the known transformations to determine the fourth, and/or first transformations.

One all of the transformations are determined, the surgical navigation system is able to determine how a view vector of the stereoscopic camera corresponds to a pose of a robotic arm. Commands entered by an operator to move the stereoscopic camera relative to its view vector are translated by the surgical navigation system using the determined transformations into movement commands for the robotic arm.

Further, as described herein, the surgical navigation system uses the determined transformations for registering patient data in the appropriate position and orientation with respect to the current view vector of the stereoscopic camera to enable the patient data to be overlaid or shown in conjunction with the live stereoscopic view. As disclosed herein, patient data includes CT data, MM data, preoperative images, and/or surgical guidance visualizations/templates.

In light of the disclosure set forth herein, and without limiting the disclosure in any way, in a first aspect of the present disclosure, which may be combined with any other aspect, or portion thereof, described herein a robotic surgical navigation system includes a robotic arm having a base section and an end-effector section. The robotic surgical navigation system also includes a stereoscopic camera connected to the end-effector section of the robotic arm and a navigation computer system communicatively coupled to the robotic arm and the stereoscopic camera. The navigation computer system is configured to determine a first transformation between the stereoscopic camera and a target surgical site using at least one camera parameter, determine a second transformation between the end-effector section and the base section based on pose data from joint sensors within the robotic arm, and determine a third transformation between the base section of the robotic arm and the target surgical site. The navigation computer system is also configured to calculate a fourth transformation using the first transformation, the second transformation, and the third transformation. The fourth transformation representing a transformation between the end-effector section of the robotic arm and the stereoscopic camera. The navigation computer system is further configured to create a correlation between a view vector of the stereoscopic camera and a pose of the robotic arm using the first transformation, the second transformation, the third transformation, and the fourth transformation. In some embodiments, the navigation computer system receives an input command from an input device with respect to the view vector of the stereoscopic camera and determines at least one robotic arm command for the robotic arm using (i) the received input command and (ii) the correlation between the view vector of the stereoscopic camera and the pose of the robotic arm. In these embodiments, the navigation computer system causes the robotic arm to move using the at least one robotic arm command.

In a second aspect of the present disclosure, which may be combined with any other aspect, or portion thereof, described herein, the at least one camera parameter includes at least one of focal lengths at different magnifications, a working distance to the target surgical site, an interpupillary distance between image sensors of the stereoscopic camera, or a zoom repeat point, and the at least one camera parameter includes information for modeling left and right image sensors of the stereoscopic as respective pinhole cameras.

In a third aspect of the present disclosure, which may be combined with any other aspect, or portion thereof, described herein, the navigation computer system is configured to determine the at least one camera parameter using a calibration target having known dimensions and an orientation placed at the target surgical site and known pixel dimensions of left and right image sensors of the stereoscopic camera.

In a fourth aspect of the present disclosure, which may be combined with any other aspect, or portion thereof, described herein, the navigation computer system is configured to determine the first transformation for a plurality of poses for the stereoscopic camera and determine the second transformation for a plurality of poses for the robotic arm.

In a fifth aspect of the present disclosure, which may be combined with any other aspect, or portion thereof, described herein, the system further comprises a coupling plate having a first side connected to the end-effector section and a second end connected to the stereoscopic camera.

In a sixth aspect of the present disclosure, which may be combined with any other aspect, or portion thereof, described herein, the first transformation includes a first $4\times4$ matrix that relates a first remote orientation and position of the target surgical site to a first local space of the stereoscopic camera, the second transformation includes a second $4\times4$ matrix that relates a second remote orientation and position of the base section to a second local space of the end-effector section of the robotic arm, the third transformation includes a third $4\times4$ matrix that relates a third remote orientation and position of the base section to a third local space of the target surgical site, and the fourth transformation includes a fourth $4\times4$ matrix that relates a fourth remote orientation and position of the end-effector of the robotic arm to a fourth local space of the stereoscopic camera.

In a seventh aspect of the present disclosure, which may be combined with any other aspect, or portion thereof, described herein, each of the $4\times4$ matrices includes a $3\times3$ rotational sub-matrix that relates the respective remote orientation to the respective local space and a $3\times1$ vector that specifies the respective remote position in a coordinate system of the respective local space, and each $3\times3$ sub-matrix includes an n-vector that projects an x-axis of the respective remote orientation to the coordinate system of the respective local space, an o-vector that projects a y-axis of the respective remote orientation to the coordinate system of the respective local space, and an a-vector a projects a z-axis of the respective remote orientation to the coordinate system of the respective local space.

In an eighth aspect of the present disclosure, which may be combined with any other aspect, or portion thereof, described herein, the navigation computer system is configured to determine the fourth transformation as a product of the first transformation, the third transformation, and an inverse of the second transformation.

In a ninth aspect of the present disclosure, which may be combined with any other aspect, or portion thereof, described herein, the pose data includes information indicative of a rotation of each joint of the robotic arm and corresponds to a position and an orientation of the robotic arm.

In a tenth aspect of the present disclosure, which may be combined with any other aspect, or portion thereof, described herein, the navigation computer system is configured to receive the third transformation as an input from an input device.

In an eleventh aspect of the present disclosure, which may be combined with any other aspect, or portion thereof, described herein, the navigation computer system is configured to determine a pose of one or more features of the target located at the target surgical site relative to the stereoscopic camera, register one or more features of the target recorded in images recorded by the stereoscopic camera to corresponding features in a pre-operative image, determine a transformation between the one or more features of the target to the pre-operative image, and determine a pose of the view vector of the stereoscopic camera in a target space as a function of the pose of the robotic arm using the transformation between the one or more features of the target to the pre-operative image and the determined correlation between the view vector of the stereoscopic camera and the pose of the robotic arm.

In a twelfth aspect of the present disclosure, which may be combined with any other aspect, or portion thereof, described herein, the input device includes at least one of a joystick, a control pad, a touchscreen, a foot pedal, or a force sensor connected to the stereoscopic camera.

In a thirteenth aspect of the present disclosure, which may be combined with any other aspect, or portion thereof, described herein, a surgical navigation method includes receiving in a navigation computer system, a request message to calibrate a robotic arm having a base section and an end-effector section, where the end-effector section connected to a stereoscopic camera via a coupling plate. The example method further includes determining, via the navigation computer system, a first transformation between the stereoscopic camera and a target surgical site using at least one camera parameter, determining, via the navigation computer system, a second transformation between the end-effector section and the base section of the based on pose data from joint sensors within the robotic arm, and calculating, via the navigation computer system, a third transformation between the base section of the robotic arm and the target surgical site, and a fourth transformation between the end-effector section of the robotic arm and the stereoscopic camera using the first transformation and the second transformation for a plurality of poses. The method further includes creating, via the navigation computer system, a correlation between a view vector of the stereoscopic camera and a pose of the robotic arm using the first transformation, the second transformation, the third transformation, and the fourth transformation. In some embodiments, the method includes receiving, in the navigation computer system from an input interface, an input command entered by an operator with respect to the view vector of the stereoscopic camera, and determining, via the navigation computer system, at least one robotic arm command for the robotic arm using (i) the received input command, and (ii)

the correlation between the view vector of the stereoscopic camera and the pose of the robotic arm. In these embodiments, the method includes transmitting from the navigation computer system the at least one robotic arm command to cause the robotic arm to move the stereoscopic camera according to the received input command.

In a fourteenth aspect of the present disclosure, which may be combined with any other aspect, or portion thereof, described herein, calculating the third transformation and the fourth transformation includes solving for, via the navigation computer system, a local minimum of a function relating the first transformation, the second transformation, the third transformation, and the fourth transformation for the plurality of poses.

In a fifteenth aspect of the present disclosure, which may be combined with any other aspect, or portion thereof, described herein, the input command includes at least one of move right, move left, move up, move down, move diagonally, move closer to the target surgical site, move further away from the target surgical site, rotate along a yaw axis, rotate along a roll axis, rotate along a pitch axis, increase a zoom magnification of the stereoscopic camera, or decrease a zoom magnification of the stereoscopic camera.

In a sixteenth aspect of the present disclosure, which may be combined with any other aspect, or portion thereof, described herein, the at least one robotic arm command includes an amount of rotation for at least one joint of the robotic arm.

In a seventeenth aspect of the present disclosure, which may be combined with any other aspect, or portion thereof, described herein, the method further includes storing to a memory device, via the navigation computer system, the correlation between the view vector of the stereoscopic camera and the pose of the robotic arm.

In an eighteenth aspect of the present disclosure, which may be combined with any other aspect, or portion thereof, described herein, the method further includes storing to a memory device, via the navigation computer system, the first transformation, the second transformation, the third transformation, and the fourth transformation.

In a nineteenth aspect of the present disclosure, which may be combined with any other aspect, or portion thereof, described herein, determining the at least one robotic arm command includes translating, via the navigation computer system, the input command into a movement delta of the view vector expressed in a coordinate system of the robotic arm using the correlation between the view vector of the stereoscopic camera and the pose of the robotic arm, determining, via the navigation computer system, new coordinates for the view vector in the coordinate system of the robotic arm using the movement delta, determining joints of the robotic arm and an amount of rotation of the determined joints for moving the view vector to the new coordinates, and creating the at least one robotic arm command based on the determined joints and the determined amount of rotation for the determined joints.

In a twentieth aspect of the present disclosure, which may be combined with any other aspect, or portion thereof, described herein, the correlation between the view vector of the stereoscopic camera and the pose of the robotic arm includes an expression of the view vector of the stereoscopic camera in a coordinate system of the robotic arm.

In a twenty-first aspect, any of the features, functionality, and alternatives described in connection with any one or more of FIGS. 2 to 16 may be combined with any of the features, functionality, and alternatives described in connection with any other of FIGS. 2 to 16.

In light of the present disclosure and the above aspects, it is therefore an advantage of the present disclosure to provide a robotic surgical navigation system that correlates a view vector of a stereoscopic camera to a coordinate system of a robotic arm to enable movement commands to be translated from a perspective of the view vector to the robotic arm coordinate space.

It is another advantage of the present disclosure to use a correlation between a view vector of a stereoscopic camera and a coordinate system of a robotic arm for registering or aligning patient data with live stereoscopic images recorded by the camera.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIG. 11 illustrates an example procedure or routine for calibrating the stereoscopic navigation system of FIGS. 2 to 8 and 10 when a Robot Base_T_Target transformation is known, according to an example embodiment of the present disclosure.

FIG. 14 illustrates an example procedure or routine for calibrating the stereoscopic navigation system of FIGS. 2 to 8 and 10 when the Robot Base_T_Target transformation is unknown, according to an example embodiment of the present disclosure.

DETAILED DESCRIPTION

Figure 1:
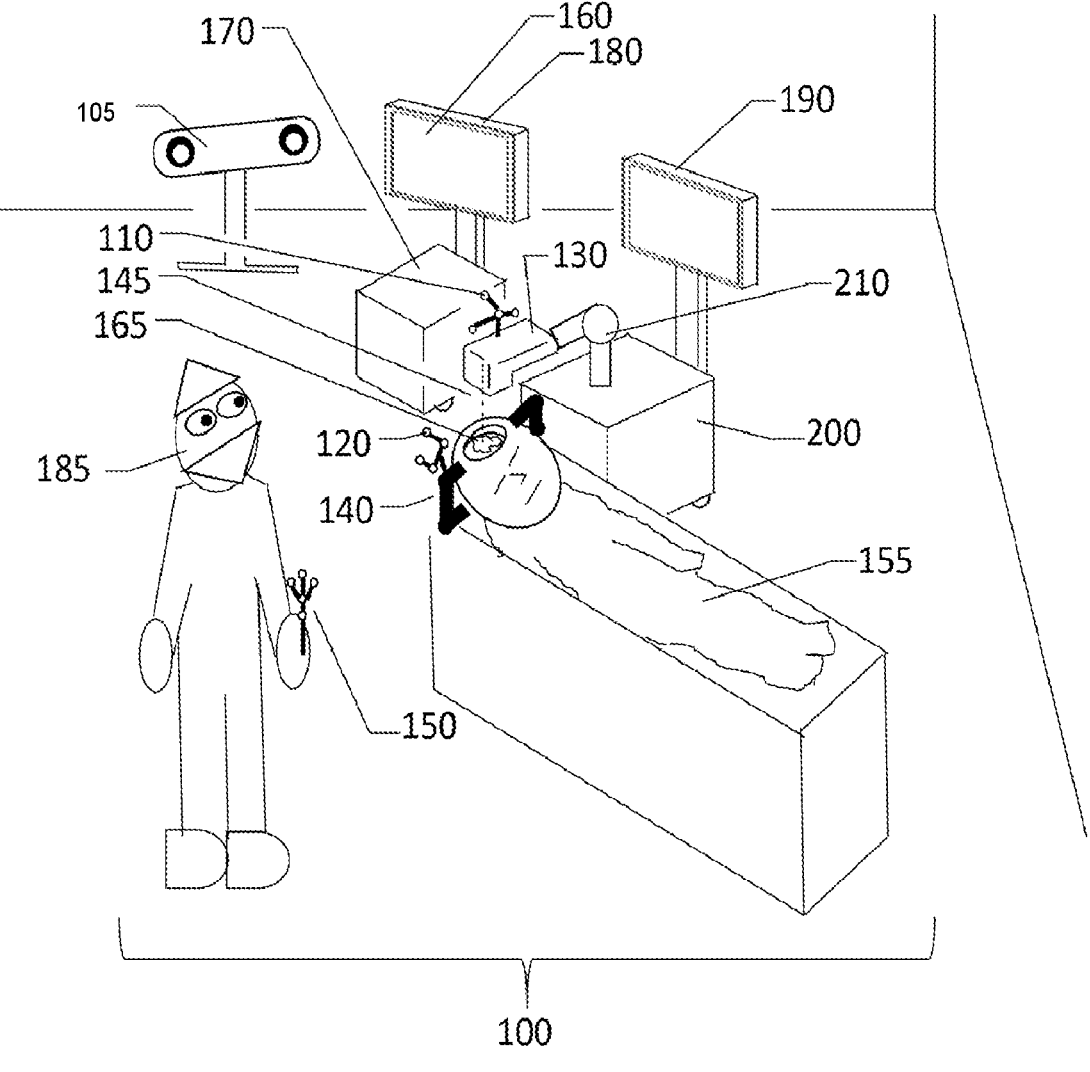
FIG. 1 shows a diagram of a known surgical navigation system, which includes a navigation camera for tracking a position of a surgical camera or microscope.

The surgical navigation system, method, and apparatus disclosed herein are configured to determine a position and/or orientation of a view vector in a patient space of a stereoscopic camera that is mechanically coupled to a robotic arm. The example surgical navigation system, method, and apparatus determine the view vector using a position and/or orientation of the robotic arm. Such a configuration enables the surgical navigation system, method, and apparatus to provide knowledge of which 3D patient anatomy is being imaged by the camera. Knowledge of the view vector enables the surgical navigation system, method, and apparatus to provide for precise control of the robotic arm and camera system in addition to registering pre-operative images, templates, or graphics to the live stereoscopic video.

The disclosure herein generally refers to microsurgery. The example surgical navigation system disclosed herein may be used in virtually any microsurgical procedure including, for example, cranial surgery, brain surgery, neurosurgery, spinal surgery, ophthalmologic surgery, corneal transplants, orthopedic surgery, ear, nose and throat surgery, dental surgery, plastics and reconstructive surgery, or general surgery.

The disclosure also refers herein to a target surgical site, scene, or field-of-view. As used herein, a target site or field-of-view includes an object (or portion of an object) that is being recorded or otherwise imaged by a stereoscopic camera. Generally the target site, scene, or field-of-view is a working distance away from a main objective assembly of the stereoscopic camera, and is aligned with the example stereoscopic camera. The target site may include a patient's biological tissue, bone, muscle, skin, or combinations thereof. In these instances, the target site may be 3D by having a depth component corresponding to a progression of a patient's anatomy.

Reference is also made throughout to an x-direction, a y-direction, a z-direction, and a tilt-direction. The z-direction is along an axis from the example stereoscopic camera to the target site, and generally refers to depth. The x-direction and y-direction are in a plane incident to the z-direction and comprise a plane of the target site. The x-direction is along an axis that is 90° from an axis of the y-direction. Movement along the x-direction and/or the y-direction refer to in-plane movement and may refer to movement of the example stereoscopic camera, movement of a robotic arm holding the stereoscopic camera, and/or movement of the target site.

In contrast to the disclosed surgical navigation system, method, and apparatus, known surgical navigation requires a bulky and costly remote (typically stereoscopic) navigation camera and support hardware in addition to a separate imaging camera. Integrating a surgical microscope to operate as a navigated probe in a traditional surgical navigation system requires trackers to be mounted on a camera/microscope head to enable the separate navigation camera to track the position and orientation of the camera/microscope head. This probe-tracking of the navigation camera/microscope head enables known surgical navigation systems to determine a position and/or orientation of the camera/microscope head's optical axis and focal point in a live surgical view and/or preoperative patient scan data, such as CT or MRI images. In other words, known navigation systems use a separate stereoscopic camera to determine a position of a camera used for imaging a patient.

FIG. 1 shows a diagram of a prior art surgical navigation system 100. As shown, the surgical navigation system 100 includes a first camera 105, which is used to determine a position of a second camera 130 (or microscope). The second camera 130 is used for imaging a patient 155 or other target surgical site. The second camera 130 is orientated with respect to a view axis or vector 145, which has a focal point 165 positioned on a portion of an anatomy of the patient 155.

Stereoscopic images recorded by the second, stereoscopic camera 130 are displayed on monitors 180 and 190. A processor 170 may register and overlay patient data on the recorded images. The patient data may include preoperative images, CT data, MM data, graphical representations of patient anatomy, and/or surgical guidance templates.

As shown in FIG. 1, trackers 110, 120, and 150 (including fiducials) are positioned respectively on a patient head clamp 140, the camera 130, and an operator 185, such as a surgeon. The patient 155 is mounted rigidly into the rigid frame of the patient head clamp 140. To enable surgical navigation, both the patient frame tracker 120 and the camera tracker 110 must be visible to the separate navigation camera 105 at all times. To preserve this line of sight for the first camera 105, the available operating volume and operating room layouts are significantly limited.

A known surgical navigation computer system 200 performs image analysis on the images recorded by the first camera 105 to determine a position and orientation of the second camera 130 relative to the patient 155 and the operator 185. The surgical navigation computer system 200 identifies the trackers 110, 120, and 150 within the recorded images. The surgical navigation computer system 200 uses known dimensions and orientations of markers or balls on each the trackers 110, 120, and 150 for comparison to the trackers 110, 120, and 150 shown in the images. The surgical navigation computer system 120 uses an identified spacing between the trackers 110, 120, and 150 in addition to an orientation of markers or balls on each of the trackers 110, 120, and 150 to determine distances, orientations, and positions of the second camera 130 relative to the patient 155 and/or the operator 185.

Additionally, a position of the patient 155 in the rigid patient head clamp 140 is determined by a registration step performed by the known surgical navigation computer system 200. This registration step relies on the remote navigation camera 105 to determine how the patient is orientated and positioned for surgery. Such registration may be affected by accuracy problems related to positioning of the remote camera 105. Further, remote positioning of the separate camera 105 relative to the patient 155 and the second camera 130 results in a large baseline for such a procedure. This large baseline reduces accuracy of the surgical navigation system 100 compared to a smaller baseline.

The known surgical navigation computer system 200 uses stereogrammetry on the stereo images received from the navigation camera 105 to determine a target position and location of the focal point 165 of the view vector 145. The surgical navigation computer system 200 correlates the target position and location of the view vector 145 with the determined position and orientation of the camera 130 relative to the patient 155 and/or the operator 185 for moving a robotic arm 210. The correlation between the view vector 145 and the determined position and orientation of the camera 130 enables movement commands to be translated into appropriate robotic arm commands. For example, a simple command to move the camera 130 "right" with respect to the view vector 145 may translate to commands for different joints of the robotic arm 210. When the commands are applied to the robotic arm, the second camera 130 ultimately moves to the "right" with respect to the view vector 145, as intended by the operator 185.

Example Surgical Navigation System

The example surgical navigation system, method, and apparatus disclosed herein eliminate the need for the reference camera 105. Instead of using a separate camera 105, the example surgical navigation system, method, and apparatus instead rigidly secure a robot reference frame to a patient reference from and perform a registration to determine the relative position and orientation between these frames. Such registration of the patient anatomy to a reference frame of interest provides more system-level accuracy.

Figure 2:
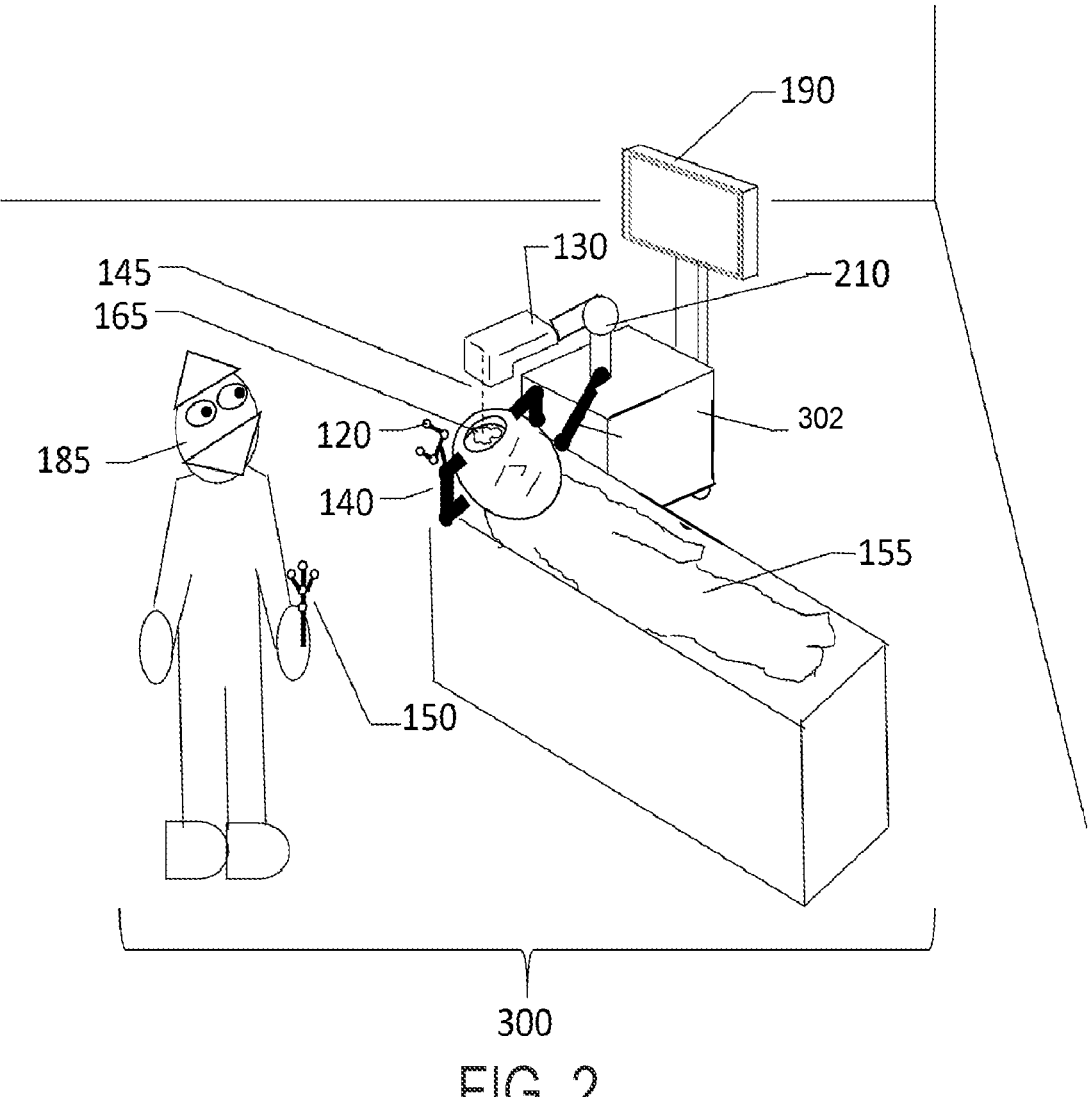
FIG. 2 shows an example stereoscopic navigation system, according to an example embodiment of the present disclosure.

FIG. 2 shows an example stereoscopic navigation system 300, according to an example embodiment of the present disclosure. In the illustrated example, the reference camera 105 from FIG. 1 is removed. A surgical navigation computer system 302 is configured to determine a relative position and/or orientation between a robot reference frame and a patient reference frame. As shown in FIG. 2, the stereoscopic navigation system 300 includes a stereoscopic digital camera 130 mounted on a robotic arm 210.

A first side of the robotic arm 210 comprises a robot end-effector, which couples to a mechanical coupling plate. A second side of the robotic arm 210 connects to a robot base. The coupling plate located at the end-effector of the robotic arm 210 is mechanically connected to the stereoscopic camera 130. The first side of the robotic arm 210 is connected to the second side via joints and links. The joints and links enable robot software and hardware on the stereoscopic navigation system 300 to position and orient the robot end-effector in many positions and orientations relative to the robot base. Sensors in the joints and/or links report the current such position and orientation at time slices (e.g. once per 8 milliseconds) back to a robot controller at the surgical navigation computer system 302 to within a high degree of precision (e.g. <100 micrometers). Universal Robots' model UR5 collaborative robot is an example of such a robotic arm 210, which can support a payload of 5 kg.

In some instances, the example stereoscopic navigation system 300 of FIG. 2 may include trackers 120 and 150, respectively, for the patient 155 and the operator 185. In other embodiments, the trackers 120 and/or 150 may be omitted. The trackers 120 and 150 may be imaged by the stereoscopic camera 130 and used by the navigation computer system 302 to provide patient and/or tool tip registration and/or tracking.

The stereoscopic camera 130 can be modeled as comprising two monoscopic cameras, with each camera corresponding to a left or right image sensor. This is not always the exact case but simplifies the discussion herein. A focal point of the stereoscopic camera 130 is a center of the stereoscopic display at some distance (referred to as a focal distance) away from the camera eye point.

Imaginary reference frames or "spaces" are used by the navigation computer system 302 in the computation of the relative position and orientation of various pieces of the whole system including the stereoscopic camera 130, the robotic arm 210, and the patient 155. An origin of a reference frame of the stereoscopic camera 130 is placed at the camera eye point. An origin of the reference frame of the robotic arm 210 is placed at a robot base. An additional reference frame is placed with its origin at the robotic arm end-effector. The orientation of each reference frame is chosen to be appropriate for its use such as enabling simpler math in the solution of relative transformations.

The origin location and orientation of a reference frame of the patient 155 includes a function of patient scan data (such as CT or Mill data), and is registered to a rigid clamp-like device, such as the patient head clamp 140, in which patient anatomy is clamped (as in traditional navigation) for the duration of the procedure. The example navigation computer system 302 uses knowledge of the position of the focal point in the patient space given only the robotic arm 210 position and orientation. This virtual representation of the robotic arm 210 location enables the navigation computer system 302 to reconstruct the patient data in the same view vector and orientation as recorded by the stereoscopic camera 130. Further, the virtual representation of the robotic arm 210 location enables navigation commands to be translated from a view vector of the stereoscopic camera 130, which points along the view from the camera eye point to its focal point, to positioning commands for the robotic arm 210.

As disclosed herein, the view vector of a given monoscopic camera is the view into the scene along a vector passing through a center of the display. For a traditional monoscopic camera with a complete set of optics, that vector is orthogonal or largely orthogonal to the plane of the display. However, for the stereoscopic camera 130, with a common main objective lens, the two monoscopic cameras share that objective lens, and it is the stereoscopic view vector that is orthogonal or largely orthogonal to the plane of the display. The view vectors of the individual cameras tilt through that center. For the following discussion, relative position and orientation of two reference frames are also known as the "relative transformation" or simply "transformation" between the two. The position and orientation of one object or reference frame relative to another is also known as a "pose."

Robotic Arm Embodiment

Figure 3:
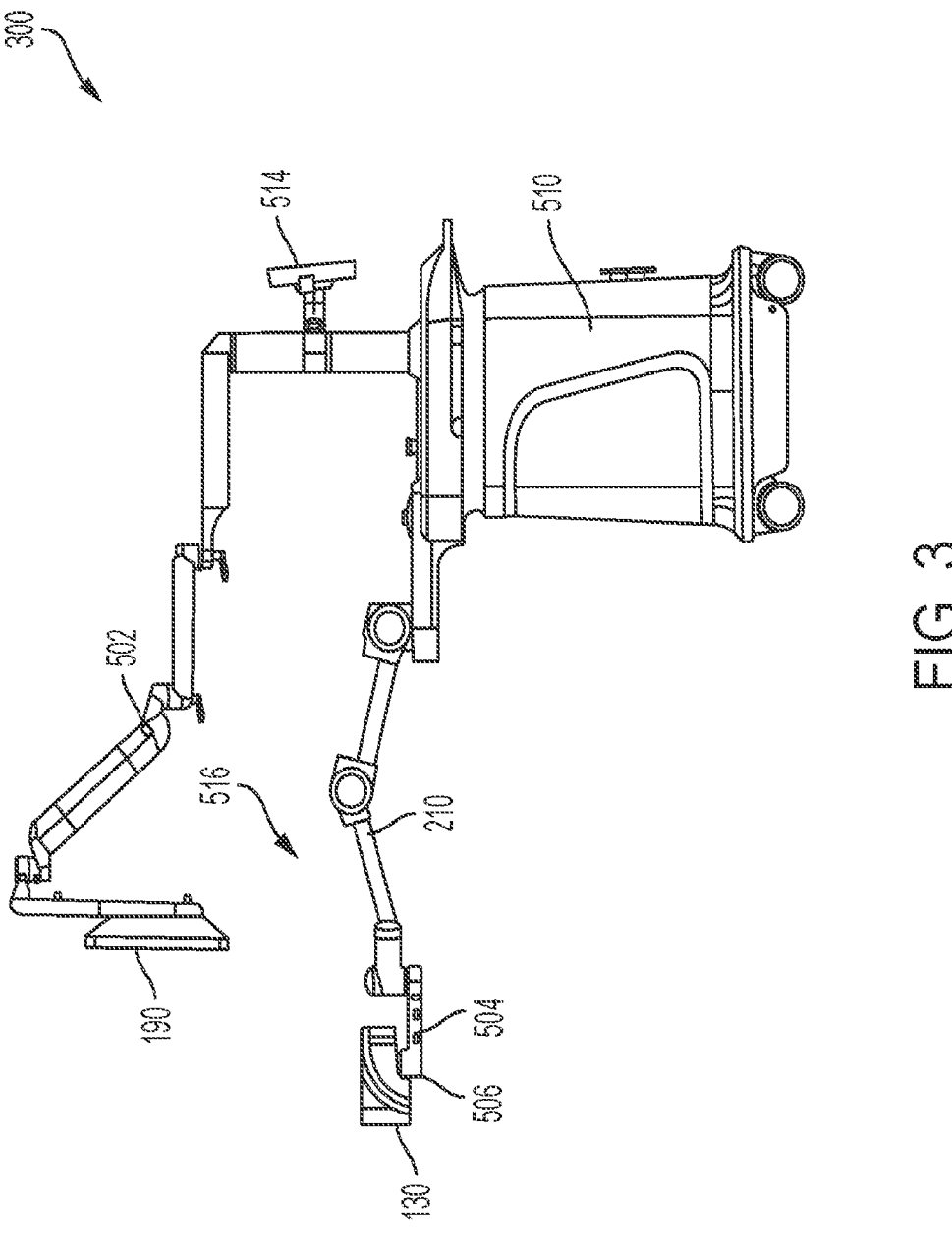
FIG. 3 shows a side view of the navigation system of FIG. 2, according to an example embodiment of the present disclosure.

FIG. 3 shows a side view of the stereoscopic navigation system 300 of FIG. 2, according to an example embodiment of the present disclosure. In the illustrated example, a display monitor 190 may be connected to a cart 510 via a mechanical arm 502 with one or more joints to enable flexible positioning. In some embodiments, the mechanical arm 502 may be long enough to extend over a patient during surgery to provide relatively close viewing for an operator. The cart 510 may house the navigation computer system 302 of FIG. 2.

As shown in FIG. 3, the display monitor 190 is positioned within a surgical environment to be easily within an operator's line of sight while performing surgery on a patient. This flexibility enables the operator to place display monitors based on personal preferences or habits. In addition, the flexibility and slim profile of the stereoscopic camera 130 reduces area consumed over a patient. The example stereoscopic visualization platform accordingly operates as an extension of the operator's eyes, enabling the operator to perform microsurgeries without dealing with the stress, restrictions, and limitations induced by previous known visualization systems.

FIG. 3 also illustrates a side view of a stereoscopic robotic platform 516, including the stereoscopic camera 130 and the robotic arm 210 of FIG. 2. The stereoscopic camera 130 is mechanically coupled to the robotic arm 210 via a coupling plate 504. In some embodiments, the coupling plate 504 may include one or more joints that provide for further degrees of positioning and or orientation of the stereoscopic camera 130. In some embodiments, the coupling plate 504 has to be manually moved or rotated by an operator. For example, the coupling plate 504 may have a joint that enables the stereoscopic camera 130 to be positioned quickly between having an optical axis along a z-axis (i.e., pointing downward toward a patient) and an optical axis along an x-axis or y-axis (i.e., pointing sideward toward a patient).

The example coupling plate 504 may include a sensor 506 configured to detect forces and/or torques imparted by an operator for moving the stereoscopic camera 130. In some embodiments, an operator may position the stereoscopic camera 130 by gripping the control arms (discussed below). After the operator has clutched the control arms with their hands, the operator may position and/or orient the stereoscopic camera 130 with assistance from the robotic arm 210. The sensor 506 detects a force vector or torque angle provided by the operator. The example stereoscopic robotic platform 516 disclosed herein uses the sensed force/torque to determine which joints of the robotic arm 210 should be rotated (and how quickly the joints should be rotated) to provide assisted movement of the stereoscopic camera 130 that corresponds to the forces/torques provided by the operator. The sensor 506 may be located at an interface between the coupling plate 504 and the stereoscopic camera 130 for detecting the forces and/or torques imparted by an operator via the control arms.

In some embodiments, the sensor 506 may include, for example, a six degrees of freedom haptic force-sensing module. In these embodiments, the sensor 506 may detect translational force or motion in the x-axis, y-axis, and z-axis. The sensor 506 may also separately detect rotational force or motion around a yaw-axis, a pitch-axis, and a roll-axis. The decoupling of the translational force and the rotational force may enable the stereoscopic robotic platform 516 to more easily calculate direct and/or reverse kinematics for control of the robot arm 210.

The example sensor 506 may be configured to detect force since the robotic arm 210 may not be movable by an operator alone. Instead, the sensor 506 detects translational and rotational force applied by an operator, which is used by the navigation computer system 302 and/or the stereoscopic robotic platform 516 to determine which joints to rotate to provide assisted movement control of the robotic arm 210. In other examples, the robotic arm 210 may permit operator movement without assistance, or at least initial assistance. In these other examples, the sensor 506 detects motion imparted by the operator, which is used by the navigation computer system 302 and/or the stereoscopic robotic platform 516 to subsequently cause one or more joints to rotate, thereby providing assisted movement. The time between initial detection of motion or the force resulting in the motion, until the navigation computer system 302 and/or the stereoscopic robotic platform 516 causes the joints to rotate may be less than 200 milliseconds ("ms"), 100 ms, 50 ms, or as few as 10 ms, where the operator does not notice the initial time of unassisted movement of the robotic arm 210.

The example sensor 506 may output digital data that is indicative of the rotational force/motion and digital data that is indicative of the translational force/motion. In this example, the digital data may have 8, 16, 32, or 64 bit resolution for the detected force/motion in each axis. Alternatively, the sensor 506 may transmit an analog signal that is proportional to the sensed force and/or motion. The example sensor 506 may transmit the data at a periodic sampling rate of, for example, 1 ms, 5 ms, 10 ms, 20 ms, 50 ms, 100, ms, etc. Alternatively, the sensor 506 may provide a near-continuous stream of force/motion data.

In some embodiments, the example sensor 506 may instead be located in one or more of the control arms or between the control arms and a housing of the stereoscopic camera 130. In examples, where each of the control arms include the sensor 506, the example navigation computer system 302 and/or the stereoscopic robotic platform 516 may receive two sets of translational and rotational force or motion. In these examples, the navigation computer system 302 and/or stereoscopic robotic platform 516 may average the values from the sensors 506.

In the illustrated embodiments, a first end of the robotic arm 210 is mounted to the cart 510 while a second, opposite end of the robotic arm is mechanically connected to stereoscopic camera 130 (e.g., the robot end effector). FIG. 3 shows the robotic arm 210 holding the stereoscopic camera 130 in an extended position, such as positioning the stereoscopic camera 130 above a surgical site while keeping the rest of the stereoscopic robotic platform 516 out of the way of an operator. The cart 510 is configured to securely hold the stereoscopic robotic platform 516 and is weighted and balanced to prevent tipping under prescribed operating positions.

Figure 4:
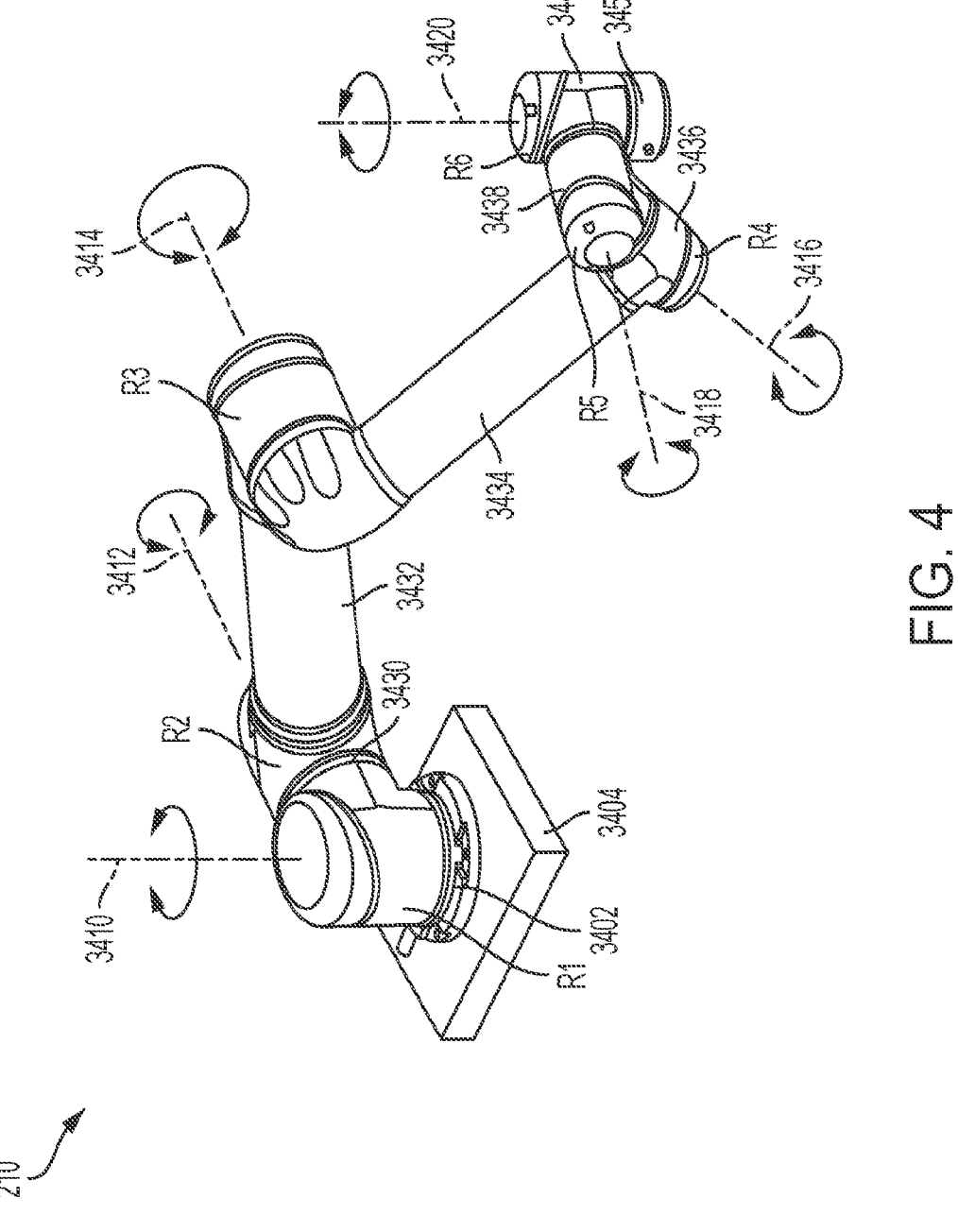
FIG. 4 illustrates an embodiment of an example robotic arm of the navigation system of FIG. 2, according to an example embodiment of the present disclosure.

FIG. 4 illustrates an embodiment of the example robotic arm 210, according to an example embodiment of the present disclosure. In some embodiments, the robotic arm 210 is similar to or comprises model UR5 from Universal Robots S/A. The exterior surfaces of the robotic arm 210 comprise aluminum and plastic materials, which are compatible for use in an operating room and easily cleaned.

While the robotic arm 210 is described herein as being electromechanical, in other examples, the robotic arm 210 may be mechanical, hydraulic, or pneumatic. In some embodiments, the robotic arm 210 may have mixed actuation mechanisms, for example, using a vacuum chuck with a control valve to hold and manipulate the stereoscopic camera 130. Further, while the robotic arm 210 is described below as including a certain number of joints and links, it should be appreciated that the robotic arm 210 may include any number of joints, any lengths of links, and/or comprise any types of joints, or sensors.

As described herein, the robotic arm 210 is situated and the joints are oriented to provide an unrestricted view of an operating field while providing a 3D stereoscopic display for an operator for any surgical procedure for a patient. Movement of the robotic arm 210 in noncritical motions is provided to be fast enough for an operator to be convenient, yet safe. Movement of the robotic arm 210 is controlled during surgery to be meticulous and accurate. In addition, movement of the robotic arm is controlled to be smooth and predictable through the entire range of motion required for a surgical procedure. As described herein, movement of the robotic arm 210 is controllable by remote control, joystick, and/or via manual manipulation of the arm itself. In some embodiments, the robotic arm 210 is configured to be positionable with minimal force (e.g., via an assisted guidance feature) with just the use of, for example, a single auricular finger.

In some embodiments, the robotic arm 210 may include mechanically or electronically locking brakes on the joints. The brakes may be engaged once the aim or "pose", which is generally the location and direction, of the stereoscopic camera 130 after it is set by an operator. The robotic arm 210 may include a locking or unlocking switch or other input device to prevent undesired manual or accidental motion. When locked, the example robotic arm provides sufficient stability that enables the stereoscopic camera 130 to provide a stable, clear image. The robotic arm 210 may additionally or alternatively include one or more dampening devices to absorb or attenuate vibrations following movement of the stereoscopic camera 130 to a new pose. The dampening devices may include, for example, fluid-filled linear or rotational dampeners, rubber-based vibration isolation mounting dampeners, and/or tuned mass—spring dampeners. Alternatively, or in addition, the robotic arm 210 may include electromechanical dampening, for example, through the use of a proportional integral derivative ("PID") servo system.

In the illustrated embodiment of FIG. 4, the robotic arm 210 includes six joints, labeled R1, R2, R3, R4, R5, and R6. In other embodiments, the robotic arm 210 may include fewer or additional joints. Additionally, in some embodiments, at least some of the joints R1 to R6 have rotational motion capabilities of +/−360°. The rotational motion may be provided by an electromechanical subsystem that includes, for each joint, an electric motor configured to drive a mechanical rotational joint through one or more anti-backlash joint gearboxes. Each of the joints R1 to R6 may include one or more rotational sensors to detect joint position. Further, each joint may include a slip clutch and/or an electromechanical brake.

Each of the joints R1 to R6 may have an overall repeatability of motion (with the stereoscopic camera 130 attached) of approximately +/−1/10 of a millimeter ("mm"). The joints may be have variable rotational speeds that can be controlled between 0.5° to 180° per second. Together, this translates to camera movement between 1 mm per second to 1 meter per second. In some embodiments, the stereoscopic robotic platform 516 may have speed governors for one or more of the joints R1 to R6 that are in place during surgical procedures. Each of the joints R1 to R6 may be electrically connected to a power source and/or command line in a controller of the robotic arm 210. Wires for power and command signals may be routed internally within the joints and links. Further, one or more of the joints may include dampeners, such as o-rings, for connection to links. The dampeners may, for example, reduce or absorb vibrations in the robotic arm 210, vibrations from the cart 510, and/or vibrations imparted via the stereoscopic camera 130.

Joint R1 includes a base joint that is mechanically coupled to a flange 3402, which is secured to a stationary structure 3404. The flange 3402 may include any type of mechanical connector. The stationary structure 3404 may include, for example, the cart 510 of FIG. 3, a wall, a ceiling, a table, etc. The joint R1 is configured to rotate around a first axis 3410, which may include the z-axis.

Joint R1 is connected to joint R2 via a link 3430. The example link 3430 includes a cylinder or other tubular structure configured to provide structural support for the downstream sections of the robotic arm 210. The link 3430 is configured to provide a rotational secure connection with joint R2 to enable joint R2 to rotate while the link 3430 is held in place by its connection to the joint R1. Joint R2 may include, for example, a shoulder joint configured to rotate around an axis 3412. The example axis 3412 is configured to be perpendicular (or substantially perpendicular) to axis 3410. The axis 3412 is configured to be within an x-y plane given the rotation of the joint R1 around the z-axis.

Joint R2 is mechanically coupled to joint R3 via link 3432. The link 3432 is configured to have a greater length than the link 3430 and is configured to provide structural support for downstream portions of the robotic arm 210. Joint R3 may include, for example, an elbow joint. Together with joint R2, joint R3 provides extensible positioning and/or orientating of the robotic arm 210. The joint R3 is configured to rotate around an axis 3414, which is perpendicular or orthogonal to the axis 3410 and parallel to the axis 3412.

Joint R3 is connected to joint R4 via link 3434, which provides structural support for downstream portions of the robotic arm 210. The example joint R4 may be, for example, a first wrist joint configured to provide rotation around axis 3416, which may be orthogonal to the axes 3412 and 3414. Joint R4 is mechanically connected to joint R5 via link 3436. Joint R5 may be a second wrist joint configured to provide rotation around an axis 3418, which is orthogonal to axis 3416. Joint R5 is mechanically connected to joint R6 via link 3438. Joint R6 may be a third wrist joint configured to rotate around axis 3420, which is orthogonal to the axis 3418. Together, the wrist joints R4 to R6 provide precise flexibility in positioning the stereoscopic camera 130 described herein.

The example robotic arm 210 includes a connector 3450. The example connector 3450 is connected to joint R6 via link 3440. In some embodiments, the example link 3440 may include a sleeve that enables joint R6 to rotate the connector 3450. As discussed herein, the connector 3450 (located at the end-effector of the robotic arm 210) may be configured to mechanically couple to the coupling plate 504 or the stereoscopic camera 130 directly when a coupling plate is not used. The connector 3450 may include one or more screws to secure the robotic arm 210 to the coupling plate 504 and/or the stereoscopic camera 130.

In some embodiments, the robotic arm 210 of the illustrated example may have a maximum reach of 85 mm, in an orientation roughly similar to a human arm. The robotic arm 210 may have a payload capacity of 5 kilograms. Further, the robotic arm 210 may be configured as a "collaborative" device to enable safe operation in the proximity of humans.

Figure 5:
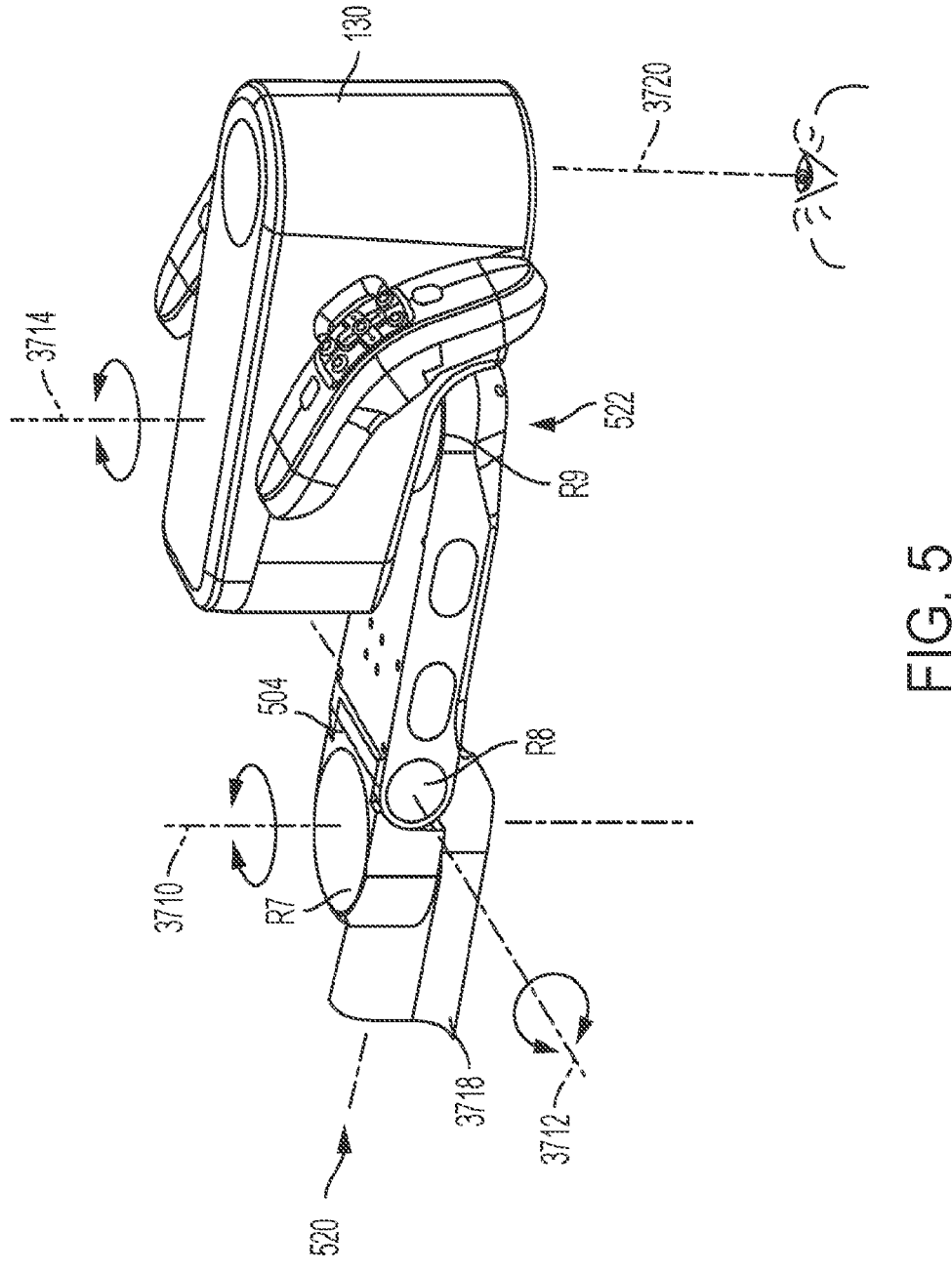
FIGS. 5 to 7 illustrate example orientations of the robotic arm and a stereoscopic camera using a coupling plate, according to example embodiments of the present disclosure.
Figure 6:
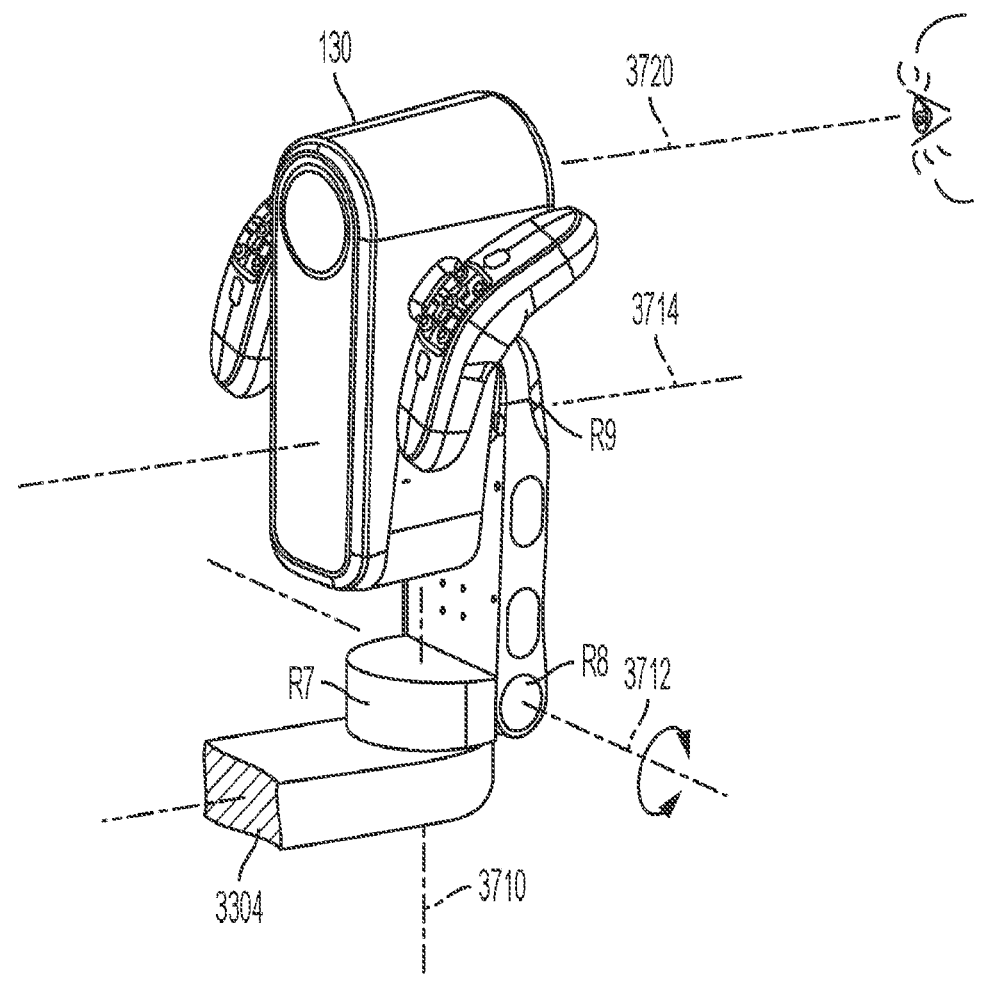
Figure 7:
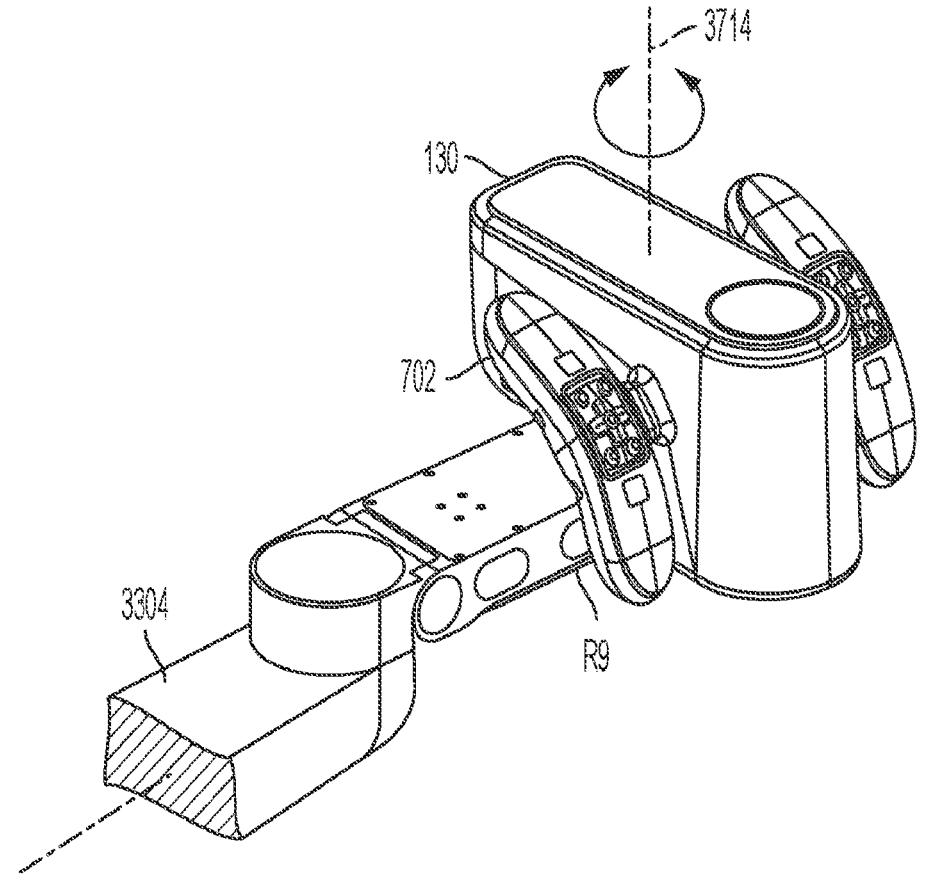

FIGS. 5 to 7 illustrate example configurations of the robotic arm 210 and the stereoscopic camera 130, according to example embodiments of the present disclosure. FIG. 5 shows an embodiment of the coupling plate 504. In the illustrated example, a first end 520 of the coupling plate 504 is connected to the connector 3450 of the robotic arm 210. A second end 522 of the coupling plate 504 is connected to the stereoscopic camera 130. The example coupling plate 504 is configured to provide additional degrees of freedom for moving the stereoscopic camera 130. The coupling plate 504 also extends the maximum reach of the robotic arm 210. The coupling plate 504 may have a length between 10 cm to 100 cm.

The coupling plate 504 may include one or more joints. In the illustrated example, the coupling plate 504 includes joints R7, R8, and R9. The example joints are mechanical joints that provide rotation around respective axes. The joints R7 to R9 may comprise rotatable latching mechanisms that are movable after an operator actuates a release button or lever. Each joint R7 to R9 may have its own release button, or a single button may release each of the joints R7 to R9. In instances where the joints R7, R8, and R9 are rotated manually by an operator, the example navigation computer system 302 may not have an accurate position and/or orientation of an end-effector of the robotic arm 210. Instead, as disclosed herein, the example navigation computer system 302 uses known positions of the robotic base, the robotic arm, and the stereoscopic camera 130 relative to a target surgical site to determine the orientation of the end-effector.

The joints R7 to R9 may be connected together via respective links. In addition, a link 3718 is provided for connection to the connector 3450 of the robotic arm 210. Joint R7 is configured to rotate around axis 3710, while joint R8 is configured to rotate around axis 3712, and joint R9 is configured to rotate around axis 3714. The axes 3710 and 3714 are parallel with each other and orthogonal to the axis 3712. Joints R7 and R9 may be configured to provide +/−360° rotation. In other examples, joints R7 and R9 may provide +/−90°, +/−180° rotation, or +/−270° rotation around the respective axes 3710 and 3714. Joint R8 may provide +/−90° rotation around the axis 3712. In some examples, joint R8 may only be set at +90°, 0°, and −90°.

In some embodiments, joints R7 to R9 may include motors that provide continuous movement. Joints R7 to R9 may also include control devices, such as switches or position sensors that communicate or provide data indicative or a rotational position. In this manner, the joints R7 to R9 may be similar to the joints R1 to R6 of the robotic arm 210 and provide for assisted movement and positioning sensing for feedback control. Power and control for joints R7 to R9 may be provided via wires routed through the robotic arm 210, power/wire connectors within the connector 3450, and/or wires external to the robotic arm 210.

FIG. 5 shows an example where the stereoscopic camera 130 is positioned in a horizontal orientation such that an optical axis 3720 is provided along a z-axis. The horizontal orientation may be used for imaging patients that are lying down. In contrast, FIG. 6 shows an embodiment where joint R8 is rotated by 90° to position the stereoscopic camera 130 in a vertical orientation such that the optical axis 3720 is provided along an x-axis or y-axis that is orthogonal to the x-axis. The vertical orientation may be used for imaging patients that are sitting. It should be appreciated that joint R8 enables the stereoscopic camera 130 to quickly be re-orientated between horizontal and vertical positions based on the procedure.

FIG. 7 shows the stereoscopic camera 130 in the horizontal orientation and rotated +90° around the axis 3714 of joint R9. FIG. 7 also shows control arms 702 of the stereoscopic camera 130. The control arms 702 include a directional input buttons that enable an operator to enter movement commands. As described herein, the movement commands are interpreted by the navigation computer system 302 with reference to the field of view and/or view axis of the stereoscopic camera 130 to provide movement as intended. Additionally or alternatively, separate control inputs, such as a joystick, may be communicatively coupled to the navigation computer system 302 and used by an operator for entering movement commands.

As illustrated in FIGS. 5 to 7, the example robotic arm 210 is configured to provide support for the stereoscopic camera 130 and allow for precise positioning and/or orientating and aiming of the camera's optical axis. Since the stereoscopic camera 130 does not have oculars and does not need to be oriented for a surgeon's eyes, there are many desirable positions and/or orientations for imaging that may be achieved that were not previously practical. A surgeon can perform with the view most optimal for a procedure rather than that most optimal for his orientation to the oculars.

The arrangement of the links and joints of the robotic arm 210 and/or the coupling plate 504, along with the motorized six (or nine) degrees of freedom generally allow the stereoscopic camera 130 to be positioned as desired with the link and joint configuration not unique to the pose of the camera. As discussed in more detail below, the joints and links of the robotic arm 210 and/or the plate 504 may be manually repositioned and/or reoriented without changing the pose or field of view ("FOV") of the stereoscopic camera 130. This configuration allows, for example, an elbow joint to be moved out of an occluding line of sight without changing the view of the surgical site through the stereoscopic camera 130. Further, the navigation computer system 302 can determine the location and pose of the stereoscopic camera 130, and calculate and display alternative positions and/or orientations of the robotic arm 210 to, for example, avoid blocking an operator's line of sight or display occlusion. Use of the various positions and/or orientations of the coupling plate 504 along with an ability of an image processor to flip, invert, or otherwise reorient the displayed image permit even more robot arm 210 positions and/or orientations.

Navigation System Transform Embodiment

Figure 8:
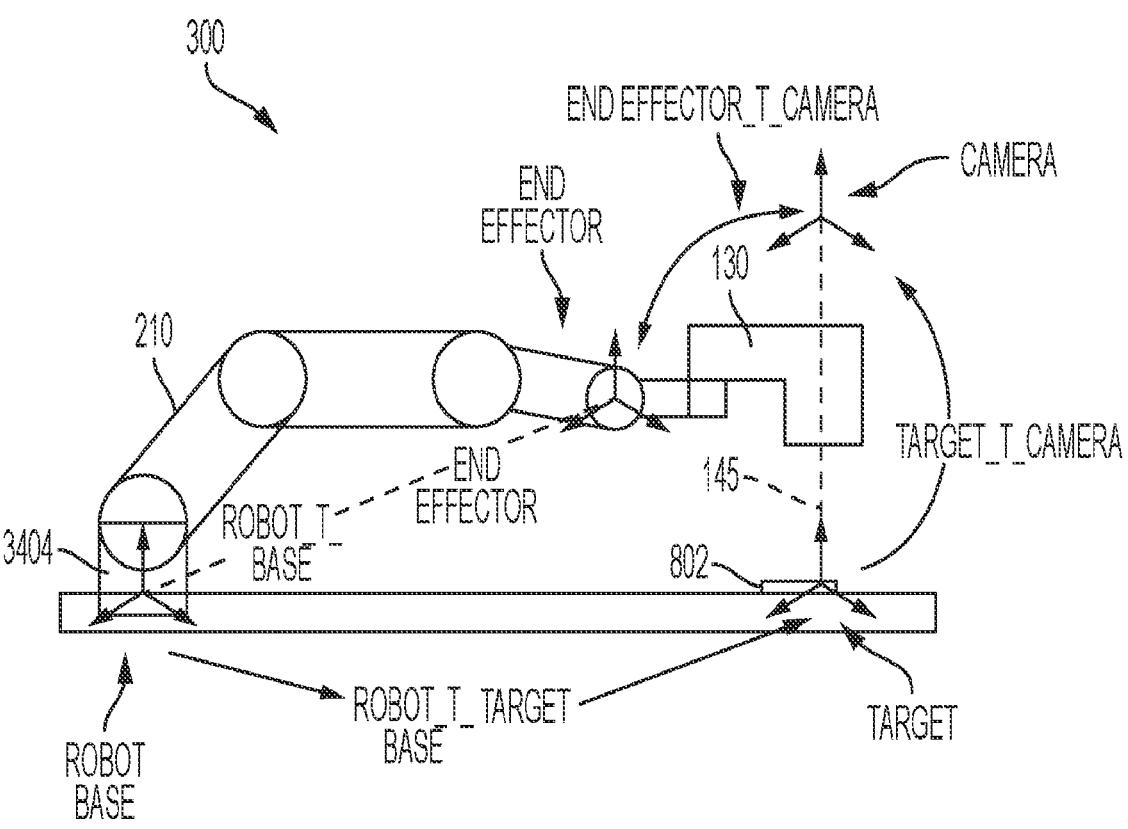
FIG. 8 is a diagram of different transformations that provide a correlation or correspondence between a stereoscopic camera, a robotic arm, and a target surgical site to enable patient data registration and operator control, according to an example embodiment of the present disclosure.

FIG. 8 is a diagram of different transformations that provide a correlation or correspondence between the stereoscopic camera 130, the robotic arm 210, and a target surgical site 802 to enable patient data registration and operator control, according to an example embodiment of the present disclosure. As shown in FIG. 8, there are four transformations. A first transformation, labeled as "Robot Base_T_Target", provides a transformation in position and orientation between the stationary structure or base 3404 of the robotic arm 210 and the target surgical site 802. In some embodiments, this transformation is known to the navigation computer system 302 as a distance and angle that is calculated between the base 3404 and the target surgical site 802. For instance, the patient frame tracker 120 on the patient may be used to calculate this distance and/or angle given the known position of the base 3404. In other embodiments, the Robot Base_T_Target is initially unknown to the navigation computer system 302.

FIG. 8 also shows a second transformation, labeled as "Robot Base_T_End-Effector". This transformation provides an end-effector position and/or orientation relative to the base 3404. The Robot Base_T_End-Effector transformation is known by the navigation computer system 302 based on rotation positions reported by sensors for each of the joints R1 to R6 of the robotic arm 210.

A third transformation is labeled as "Target_T_Camera". The Target_T_Camera is another transformation that is known by the navigation computer system 302. The navigation computer system 302 may use intrinsic and/or extrinsic parameters to determine a pose (e.g., a position and/or orientation) of the stereoscopic camera 130 relative to the target surgical site 802. The example navigation computer system 302 is configured to use the intrinsic and/or extrinsic parameters to align live stereoscopic images with patient data, including one or more images/models. The mapping of the intrinsic and/or extrinsic parameters enables the navigation computer system 302 to create a mathematical model of the stereoscopic camera 130 that is implemented in software, firmware, hardware, and/or computer code. In an example, the navigation computer system 302 is configured to receive, determine, or access camera model parameters.

Figure 9:
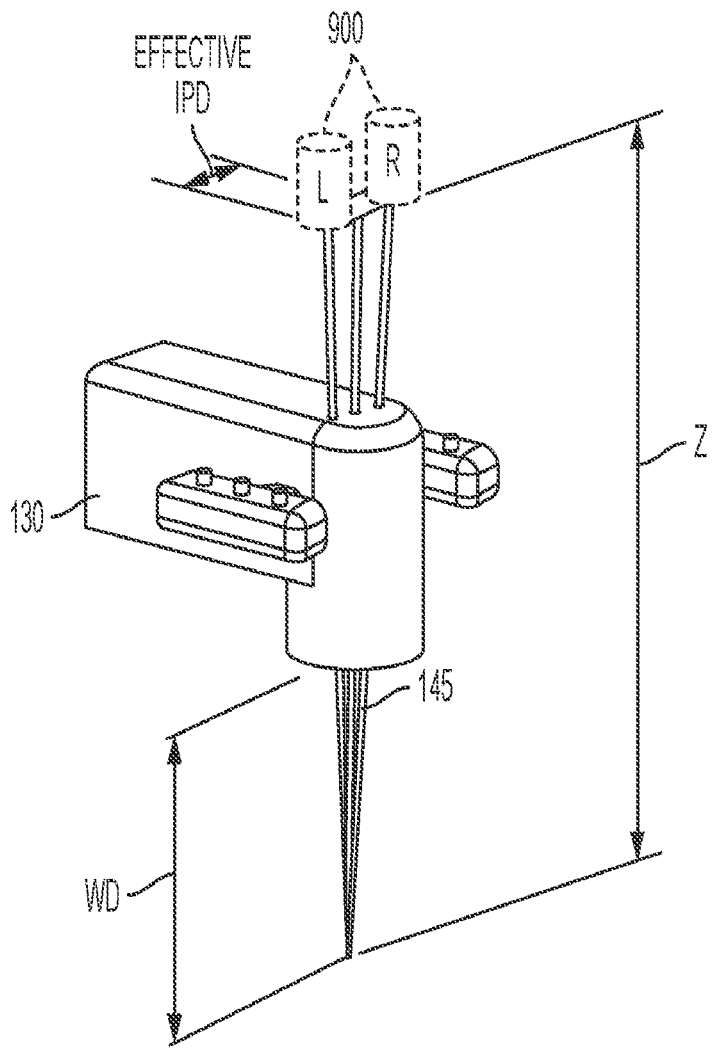
FIG. 9 illustrates a diagram of a calibrated stereoscopic camera in which the optical intrinsic and/or extrinsic parameters are fully characterized, according to an example embodiment of the present disclosure.

FIG. 9 illustrates a diagram of a calibrated stereoscopic camera 130 in which the optical intrinsic and/or extrinsic parameters are fully characterized, according to an example embodiment of the present disclosure. In the illustrated embodiment, the left and right optical axes are shown leading to imaginary left and right image sensor positions 900, as determined via a camera model. FIG. 9 also shows the central stereoscopic optical axis or view vector 145, which is provided at a focal point having a working distance ("WD") from the stereoscopic camera 130. The imaginary left and right view components of the camera models are positioned at a focal distance Z. In addition, the left and right view components of the camera models are spaced apart by the measured, effective interpupillary distance ("IPD"). In the illustrated example, an object at the focal plane (e.g., the target surgical site 802) is viewed with similar stereoscopic perspective by the imaginary left and right view components as recorded by image sensors within the stereoscopic camera 130.

Returning to FIG. 8, a fourth transformation, labeled "End-Effector_T_Camera," is not known by the navigation computer system 302. The End-Effector_T_Camera transformation corresponds to an orientation and/or position of the stereoscopic camera 130 to the end-effector of the robotic arm 210 and/or the coupling plate 504. The End-Effector_T_Camera transformation may be unknown to the navigation computer system 302 due to manual rotation of the coupling plate 504. Further, the End-Effector_T_Camera transformation may be unknown to the navigation computer system 302 due to mechanical tolerances of the robotic arm 210 and/or the coupling plate 504, sag of the robotic arm 210, and/or movement of parts internal to the stereoscopic camera 130.

Unless the End-Effector_T_Camera transformation is determined, the navigation computer system 302 is not able to correctly translate movement commands from an operator into movement of the robotic arm 210. Further, the navigation computer system 302 is not able to properly register patient data with the view vector 145 unless the End-Effector_T_Camera transformation is determined. The sections below describe how the navigation computer system 302 determines the End-Effector_T_Camera transformation when the Robot Base_T_Target transformation is unknown and known.

Surgical Navigation Computer Embodiment

Figure 10:
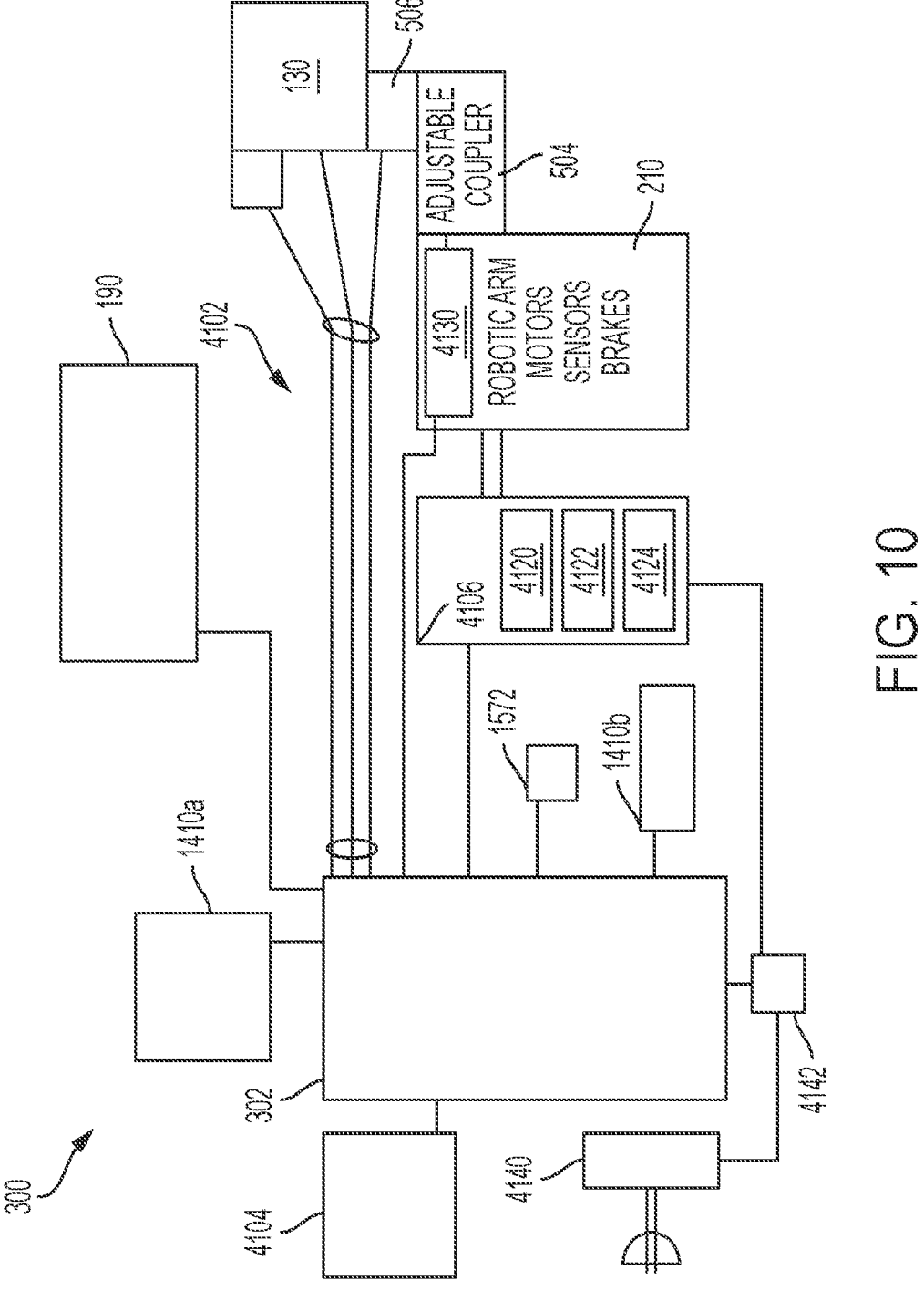
FIG. 10 illustrates an embodiment of the stereoscopic navigation system of FIGS. 3 to 8, according to an example embodiment of the present disclosure.

FIG. 10 illustrates an embodiment of the stereoscopic navigation system 300 of FIGS. 3 to 8, according to an example embodiment of the present disclosure. The example stereoscopic navigation system 300 includes the stereoscopic camera 130. In the illustrated embodiment, the stereoscopic navigation system 300 includes the navigation computer system 302, which is located remote from the stereoscopic camera 130. The navigation computer system 302 may include, for example, a processor, a laptop computer, a workstation, a desktop computer, a tablet computer, a smartphone, etc., configured with one or more software programs defined by instructions stored in a memory 1570 that, when executed by the navigation computer system 302, cause the navigation computer system 302 to perform the operations described herein. The example navigation computer system 302 in this example is configured to include (or perform the operations described in connection with) an information processor module 1408, an image sensor controller 1502, and/or a motor and lighting controller 1520.

The navigation computer system 302 is electrically and/or communicatively coupled to the stereoscopic camera 130 via a wire harness 4102. In some embodiments, the harness 4102 may be external to the robotic arm 210. In other embodiments, the wire harness 4102 may be internal or routed through the robotic arm 210. In yet other embodiments, the stereoscopic camera 130 may communicate wirelessly with the navigation computer system 302 via Bluetooth®, for example. The example navigation computer system 302 is also electrically and/or communicatively coupled to the sensor 506 via the wire harness 4102.

In the illustrated example, the navigation computer system 302 is further communicatively coupled to at least one of a display monitor 190, input devices 1410a, 1410b, and other devices/systems 4104 (e.g., medical imaging devices such as an X-ray machine, a CT machine, an Mill machine, a camera, a workstation for storing images, or surgical guidelines, etc.). The input device 1410a may include a touch screen device, and the input device 1410b may include a foot switch. The touch screen input device 1410a may be integrated with the display monitor 190 and/or provided as a separate device on, for example, the cart 510 of FIG. 3. The example display monitor 190 is configured to display one or more user interfaces that include a stereoscopic video (or separate two-dimensional left and right videos) of a target surgical site imaged by the stereoscopic camera 130.

The touch screen input device 1410a is configured to provide one or more user interfaces for receiving user inputs related to the control of the stereoscopic camera 130, the coupling plate 504, and/or the robotic arm 210. The input device 1410a may include one or more graphical control buttons, sliders, etc., that are configured to enable an operator to specify, set, or otherwise provide instructions for controlling a working distance, focus, magnification, source and level of illumination, filters, and/or digital zoom of the stereoscopic camera 130. The input device 1410a may also include one or more control buttons to enable an operator to select surgical guidance graphics/text, a video, and/or an image for fusing and/or otherwise superimposing on the displayed stereoscopic video displayed on the display monitor 190. The input device 1410a may also include a user interface that is configured to enable an operator input or create a surgical procedure visualization template. The input device 1410a may further include one or more control buttons for controlling the robotic arm 210 and/or the coupling plate 504, including options for controlling operational parameters such as speed, motion, deployment/stowing, calibration, target-lock, storing a view position, and/or changing or inputting a new orientation of the stereoscopic camera 130. The user interface controls for the robotic arm 210 and/or the coupling plate 504 may include controls for moving the stereoscopic camera 130, which are translated into commands for the individual joints R1 to R9. Additionally or alternatively, the user interface controls for the robotic arm 210 and/or the coupling plate 504 may include controls for moving each of joints R1 to R9 individually. Inputs received via the input device 1410a are transmitted to the navigation computer system 302 for processing.

The example foot plate input device 1410b may include, for example, a food pedal configured to receive inputs for controlling a position of the stereoscopic camera 130, the coupling plate 504, and/or the robotic arm 210. For example, the foot plate input device 1410b may include controls for moving the stereoscopic camera 130 along the x-axis, the y-axis, and/or the z-axis. The foot plate input device 1410b may also include controls for storing a position of the stereoscopic camera 130 and/or returning to a previously stored position. The foot plate input device 1410b may further include controls for changing a focus, zoom, magnification, etc., of the stereoscopic camera 130.

In other embodiments, the stereoscopic navigation system 300 may include additional and/or alternative input devices 1410, such as a joystick, mouse, or other similar 2D or 3D manual input device. The alternative input devices 1410 are configured to provide inputs similar to an X-Y panning device, with additional degrees of freedom resulting in flexibility of system motion. Input devices with 3D capabilities, such as a 3D mouse or six degrees of freedom controller are well suited for flexible and convenient input commands. A major benefit of these user control devices is that the surgical image can be easily viewed while the motion is occurring. Further, an operator can view what is happening around the entire surgical and nearby sites to avoid, for example, bumping the stereoscopic camera 130 into surgical staff and/or nearby equipment.

Optionally, the alternative input devices 1410 may include a head, eye, or glasses-mounted tracking device; a voice recognition device; and/or a gesture input device. These types of alternative input devices 1410 facilitate "hands-free" operability such that an operator does not need to touch anything with their sterile gloves. A gesture-recognizing control may be used, where certain operation hand motions are recognized and translated into control signals for the stereoscopic camera 130, the coupling plate 504, and/or the robotic arm 210. A similar function is provided by a voice-recognition device, where a microphone senses a command from an operator, such as "move the camera left," recognizes the speech as a command, and converts it into appropriate camera and/or robot control signals.

Other embodiments include a device configured to track a position of an operator's head (via for example a trackable target or set of targets that are mounted on an operator's 3D glasses) in a frame of reference and a footswitch to activate "head tracking." The example tracking input device is configured to store a starting position of an operator's head at activation time and then detects head position continually at some short time interval. The tracking input device in conjunction with the navigation computer system 302 may calculate a movement delta vector between a current position and the starting position and convert the vector into corresponding robotic arm or camera lens movements. For example, an alternative tracking input device 1410 and the navigation computer system 302 may convert left/right head movements into robotic arm movements such that an image onscreen moves left/right. The alternative tracking input device 1410 and the navigation computer system 302 may also convert up/down head movements into robotic arm or camera lens movements such that an image onscreen moves up/down, and may convert forward/back head movements into robotic arm or camera lens movements such that an image onscreen zooms in/out. Other movement conversions are possible, for example, by converting head rotation into a "lock-to-target" motion of the robotic arm 210. As described here, lock-to-target is configured to maintain a focal point of the stereoscopic robotic platform 516 on the same point in a scene or FOV to within some tolerance and pivot the robotic arm 210 (and hence the view) in a direction which mimics the head movement of an operator.

In the illustrated example, the stereoscopic navigation system 300 of FIG. 10 includes a robotic arm controller 4106 that is configured to control the robotic arm 210 and/or the coupling plate 504. The robotic arm controller 4106 may include a processor, a server, a microcontroller, a workstation, etc., configured to convert one or more messages or instructions from the navigation computer system 302 into one or more messages and/or signals that cause any one of joints R1 to R9 to rotate. The robotic arm controller 4106 is also configured to receive and convert sensor information, such as joint position and/or speed from the robotic arm 210 and/or the coupling plate 504 into one or more messages for the navigation computer system 302.

In some embodiments, the robotic arm controller 4106 is configured as a stand-alone module located between the navigation computer system 302 and the robotic arm 210. In other embodiments, the robotic arm controller 4106 may be included within the robotic arm 210. In yet other embodiments, the robotic arm controller 4106 may be included with the navigation computer system 302.

The example robotic arm controller 4106 includes one or more instructions stored in a memory 4120 that are executable by a robotic processor 4122. The instructions may be configured into one or more software programs, algorithms, and/or routines. The memory 4120 may include any type of volatile or non-volatile memory. The example robotic processor 4122 is communicatively coupled to the navigation computer system 302 and is configured to receive one or more messages related to operation of the robotic arm 210 and/or the coupling plate 504. The example robotic processor 4120 is also configured to transmit to the navigation computer system 302 one or more messages that are indicative of positions and/or speeds of joints R1 to R9. The one or more messages may also be indicative that a joint has reached a travel-stop or is being prevented from moving.

The example processor 4120 is configured to determine which joints R1 to R9 are powered in a coordinated manner such that a totality of all motions of all the joints result in the desired image motion at the stereoscopic camera 130. In a "move the camera left" example, there may be complex motions of several joints which cause the camera's surgical image to appear to simply and smoothly translate to the left, from a relative viewpoint of an operator. It should be noted that in the "move the camera left" example, depending on how the stereoscopic camera 130 is connected to the robotic arm 210 through the coupling plate 504, the control signals to specific joints may be drastically different depending on the position/orientation.

The memory 4120 may include one or more instructions that specify how joints R1 to R9 are moved based on a known position of the joints. The robotic arm controller 4106 is configured to execute the one or more instructions to determine how instructed camera movement is translated into joint movement. In an example, the robotic arm controller 4106 may receive messages from the navigation computer system 302 indicative that the stereoscopic camera 130 is to move downward along a z-axis and move sideward in an x-y plane. In other words, the navigation computer system 302 transmits indicative of inputs received via the input devices 1410 (translated based on the above-described transformations) regarding desired movement of the stereoscopic camera 130. The example robotic arm controller 4106 is configured to translate the vectors of movement in 3-dimensional coordinates into joint position movement information that achieves the desired position/orientation. The robotic arm controller 4106 may determine or take into account the current location of the links and joints of the robotic arm 210 and/or the coupling plate 504 (and/or a position/orientation of the stereoscopic camera 130) in conjunction with the desired movement to determine a movement delta vector. In addition, the robotic arm controller 4106 may perform one or more checks to ensure the desired movement does not cause the stereoscopic camera 130 to enter into or progress close to a restricted area, as specified by one or more 3D boundaries that are defined in the same coordinate system as the robotic arm 210 and coupling plate

504. Areas close to a boundary may specify a reduced scale factor that is applied by the robotic arm controller 4106 when movement signals are sent to the joints, which causes the joints to move slower as the robotic arm 210 approaches a boundary, and not move any further past a boundary.

After the boundary checks are performed, the robotic arm controller 4106 uses the movement delta and the current position/orientation of each of joints R1 to R9 to determine an optimal or near optimal movement sequence for rotating one or more of the joints to cause the robotic arm 210 to move the stereoscopic camera 130 into the specified location. The robotic arm controller 4106 may use, for example, an optimization routine that determines a minimal amount of joint movement needed to satisfy the movement delta vector. After the amount of joint movement is determined, the example robotic arm controller 4106 is configured to send one or more messages (indicative of an amount of rotation and speed of rotation, taking into account any scale factors) to a motor controller 4124. The robotic arm controller 4106 may transmit a sequence of messages to cause the robotic arm 210 and/or coupling plate 504 to move in a defined or coordinated sequence. The sequence of messages may also cause a change in joint speed as, for example, the robotic arm 210 approaches a virtual or physical boundary.

The example motor controller 4124 is configured to translate or covert the received messages into analog signals, such as pulse-width modulated ("PWM") signals that cause one or more of joints R1 to R9 to rotate. The motor controller 4124 may select, for example, the input line to the appropriate joint motor, where a pulse duration is used for controlling a duration of time that the motor rotates and a frequency, duty cycle, and/or amplitude of the pulse is used to control rotation speed. The motor controller 4124 may also provide power for the joint motors and corresponding joint sensors.

In some embodiments, the robotic arm controller 4106 in combination with the motor controller 4124 are configured to receive or read joint sensor position information (e.g., pose data) and determine, through kinematics, the location and orientation of the robotic joints and stereoscopic camera 130. Each joint R1 to R9 may include at least one sensor that detects and transmits data indicative of joint position, joint rotational speed, and/or joint rotational direction. In some embodiments, the sensors transmit only position information and speed/direction are determined by the robotic arm controller 4106 based on differences in the position information over time. The robotic arm controller 4106 may transmit the sensor data to the navigation computer system 302 for determining movement and/or transformation information related to the robotic arm 210.

The robotic arm controller 4106 receives movement instructions from the navigation computer system 302 and determines, through Jacobian, forward, and/or inverse kinematics, which motors and joints should be activated, how fast and how far, and in what direction. The robotic arm controller 4106 then sends the appropriate command signals to motor power amplifiers in the motor controller 4124 to drive the joint motors in the robotic arm 210.

The example robotic arm 210 receives appropriate motor power signals and moves accordingly. Sensors and brakes in the robotic arm 210 react to the various operations and feedback information from the robotic arm controller 4106. In some embodiments, the robotic arm 210 is mechanically and communicatively connected to the coupling plate 504, which transmits coupler status and orientation information to the robotic arm controller 4106.

In some embodiments, the example robotic arm 210 of FIG. 10 includes a coupler controller 4130. The example coupler controller 4130 is configured to bypass the robotic processor 4106 and relay control information between the navigation computer system 302 and the coupling plate 504. The coupler controller 4130 may receive messages from the navigation computer system 302, and correspondingly cause joints R7 to R9 rotate on the coupling plate 504. The coupler controller 4130 may also receive sensor information regarding joint position and/or speed and transmit one or more messages to the navigation computer system 302 indicative of the joint position and/or speed. In these embodiments, the navigation computer system 302 may transmit messages for controlling the robotic arm 210 and separate messages for the coupling plate 504.

In some embodiments, the robotic arm controller 4106 is configured to determine how joints R7 to R9 are to move. However, if the coupling plate 504 is not communicatively coupled directly to the robotic arm 210, the robotic processor 4106 may transmit the movement signals to the coupler controller 4130 via the navigation computer system 302. In instances where at least some operators of the robotic processor 4106 are located with the processor 4102, the coupler controller 4130 receives movement commands or signals from the navigation computer system 302 in conjunction with the robotic arm 210 receiving movement commands or signals from the navigation computer system 302.

In the illustrated embodiment of FIG. 10, the example stereoscopic camera 130, the navigation computer system 302, the coupling plate 504, the robotic arm 210, the robotic arm controller 4106, and/or the input devices 1410 receive power via an input power module 4140. The example input power module 4140 includes a power supply (such as power from a wall outlet) and/or an isolation transformer to prevent powerline anomalies from disrupting system performance. In some instances, the power supply can include a battery power supply.

The stereoscopic navigation system 300 may also include an emergency stop switch 4142 that is configured to immediately cut off power. The switch 4142 may only cutoff power to the robotic arm 210 and/or the coupling plate 204. The processor 4106 may detect activation of the emergency stop switch 4142 and cause joint brakes to engage to prevent the robotic arm 210 from falling. In some instances, the robotic arm 210 is configured to activate the joint brakes after detecting a loss of power. In some embodiments, joints R1 to R6 of the robotic arm 210 are configured to slip if a force above a threshold is applied, thereby enabling an operator to quickly move the arm out of the way in an emergency, with or without power.

In some embodiments, the navigation computer system 302 operates in connection with the robotic arm controller 4106 to adjust one or more lenses of the camera based on or in cooperation with movement of the robotic arm 210 and/or the coupling plate 504. For example, if the robotic arm 210 is moved toward a surgical site, the navigation computer system 302 operates in connection with the robotic arm controller 4106 to change a working distance or focal point by moving one or more of the lenses of the stereoscopic camera 130 to maintain focus. The navigation computer system 302 operates in connection with the robotic arm controller 4106 to determine, for example, that movement of the robotic arm 210 causes a working distance to decrease. The navigation computer system 302 operates in connection with the robotic arm controller 4106 to determine a new position for the lenses based on the new working distance set by moving the robotic arm 210. This may include moving one or more lenses for adjusting focus. In some embodiments, the navigation computer system 302 may instruct the stereoscopic camera 130 to operate a calibration routine for the new position of the robotic arm 210 to eliminate, for example, spurious parallax.

Surgical Navigation System Calibration Embodiments

The example navigation computer system 302 performs a calibration to determine the unknown transformations described above. The calibration is performed prior to a surgical procedure. For instance, the calibration may be performed after an operating room is prepared and the stereoscopic navigation system 300 is positioned. The described calibration may determine, for example, a transformation between the robot arm 210 (e.g., a robotic frame) and a frame of each of the modeled monoscopic cameras of the stereoscopic camera 130.

FIG. 11 illustrates an example procedure 1100 or routine for calibrating the stereoscopic navigation system 300, according to an example embodiment of the present disclosure. Although the procedure 1100 is described with reference to the flow diagram illustrated in FIG. 11, it should be appreciated that many other methods of performing the steps associated with the procedure 1100 may be used. For example, the order of many of the blocks may be changed, certain blocks may be combined with other blocks, and many of the blocks described are optional. Further, the actions described in procedure 1100 may be performed among multiple devices including, for example, the navigation computer system 302, the robotic arm 210, and/or the stereoscopic camera 130. For example, the procedure 1100 may be performed by a program stored in the memory device that is communicatively coupled to or part of the navigation computer system 302.

In some embodiments, the coupling plate 504 is connected to the robotic arm 210 (block 1102). If a coupling plate 504 is not used, the stereoscopic camera 130 is connected directly to the connection or coupling interface connector 3450 of the robotic arm 210. If the coupling plate 504 is used, the stereoscopic camera 130 is connected to the coupling plate 504 (block 1104). As discussed above, the first end 3702 of the coupling plate 504 is connected to the robotic arm 210 and the second end 3704 of the coupling plate 504 is connected to the stereoscopic camera 130.

Figure 12:
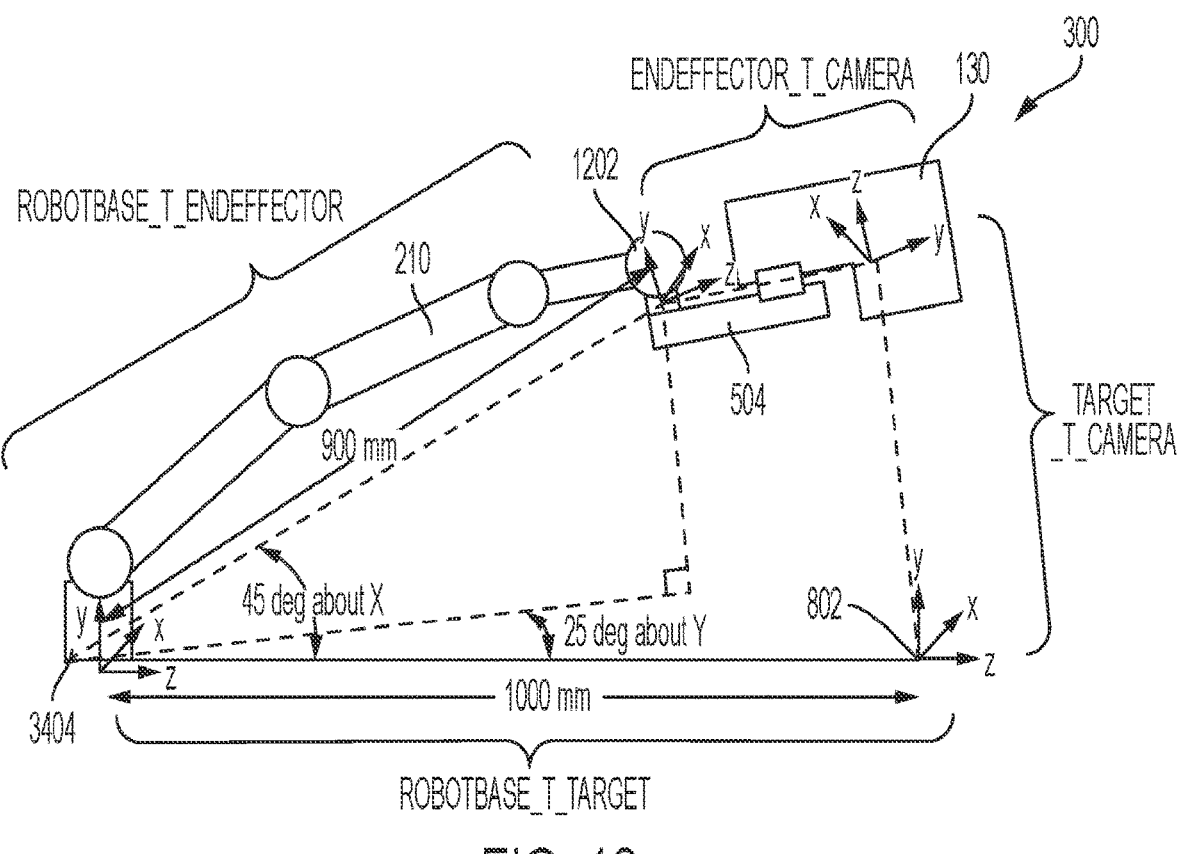
FIG. 12 shows a diagram that is illustrative of transformations between a robotic arm, a stereoscopic camera, and a target surgical site, according to an example embodiment of the present disclosure.

After connection of the stereoscopic camera 130, the example procedure 1100 continues by determining a Target_T_Camera transformation (block 1106). As discussed above, the Target_T_Camera transformation describes a difference in pose (e.g., orientation and position) between the stereoscopic camera 130 and a target surgical site. FIG. 12 shows a diagram that is illustrative of the Target_T_Camera transformation between the stereoscopic camera 130 and the target surgical site 802, according to an example embodiment of the present disclosure.

Using the robotic arm 504, the navigation computer system 302 poses the stereoscopic camera 130 to view a calibration device placed at the target surgical site. The navigation computer system 302 records an image recorded by left and right imaging sensors of the stereoscopic camera 130, as shown in FIG. 9. The navigation computer system 302 then moves the stereoscopic camera 130 and robotic arm 210 through a sufficient number of such poses, such as ten different poses. At each pose, the navigation computer system 302 records left and right images from the stereoscopic camera 130. The navigation computer system 302 then performs a calibration routine, such as the OpenCV camera calibration routine calibrateCamera.

In the example, the calibration device may include an 8×8 chessboard, which has a known layout and dimensions. For example, each of the squares of the chessboard has known length and width dimensions of 2 millimeters. In other embodiments, a different calibration device with known dimensions and layout may be used. In the embodiment example using the chessboard, the example navigation computer system 302 is also programmed with known dimensions of pixels of the left and right image sensors (e.g. 2.2 micrometers square). This example, the calibration device includes features that are extractable by computer vision techniques. The calibration device remains rigid during the time of camera calibration. Further, the calibration device may include a feature or features of known dimensions visible to the camera 130 in at least several of the images recorded for the purpose of calibration. The features are sufficient to establish a coordinate system of the calibration target. Such a coordinate system is established, for example, by two line segments joined at one end and perpendicular to each other each. The line segments have a known length, with one segment being designated along an X-axis of the coordinate system and the other segment being designated along a Y-axis of the coordinate system. The coordinate system may be designated as a right-handed coordinate system.

For each of the poses, the navigation computer system 302 creates a correspondence between the known calibration device and a coordinate system of the camera. The navigation computer system 302 estimates a distance from the calibration device using known dimensions of pixels to calculate a perceived size of the squares on the chessboard, and compare the calculation to the known size of the chessboard squares. Further, the navigation computer system 302 is able to determine an angle or orientation of the camera relative to the target based on differences in sizes of the perceived squares, where squares further away from the stereoscopic camera 130 have a smaller size compared to closer squares.

The navigation computer system 302 provides a calibration output that includes an estimate of intrinsic parameters (e.g., a focal length at different magnifications, working distance, interpupillary distance between image sensors, zoom repeat point, etc.) of the stereoscopic cameras 130 in addition to a correlation between poses of the image sensors for each pose of the stereoscopic camera 130. The intrinsic camera parameters are known as an intrinsic matrix and include sufficient information to model a given monoscopic camera and its sensor as a pinhole camera and to improve upon that model with a set of optical distortion parameters which are then used to correct such distortions. Such intrinsic information provides for the determination of the stereoscopic camera 130 relative to the target surgical site 802. The pose of the stereoscopic camera 130 relative to the target surgical site 802 is specified by the navigation computer system 302 in one or more extrinsic 4×4 matrix (matrices), which is the Target_T_Camera transformation.

Figure 13:
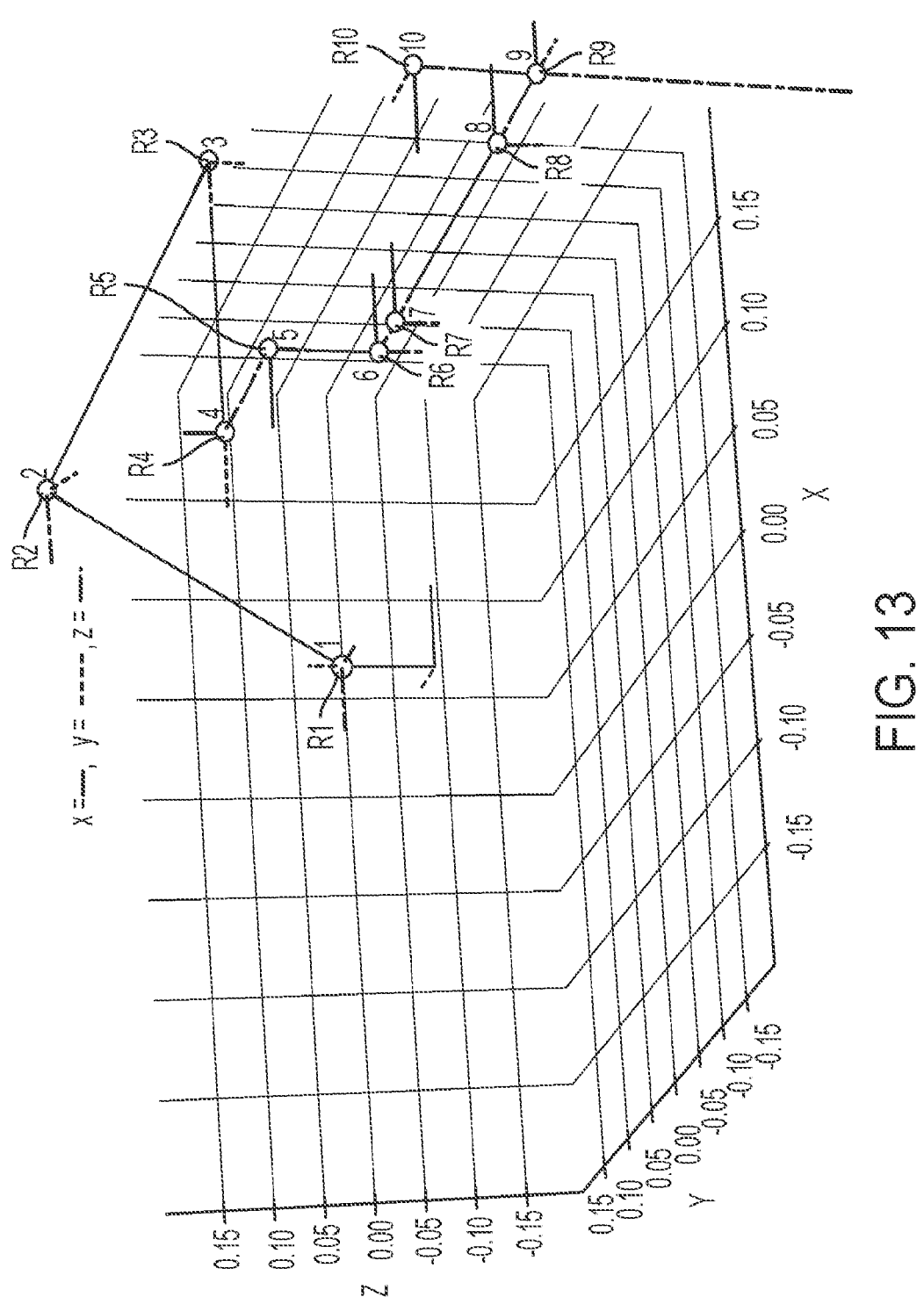
FIG. 13 shows a diagram that is illustrative of robot space for determining a Robot Base_T_End-Effector transformation, according to an example embodiment of the present disclosure.

The example procedure of FIG. 11 continues by the navigation computer system 302 determining the Robot Base_T_End-Effector transformation (block 1108). FIG. 13 shows a diagram that is illustrative of robot space for determining the Robot Base_T_End-Effector transformation, according to an example embodiment of the present disclosure. The example navigation computer system 302 reads joint positions of the robotic arm 210 from the robotic arm controller 4106. The different joint positions provide indications of linkage positions to enable the navigation computer system 302 to determine a pose of an end-effector 1202 of the robotic arm 210 relative to the base 3404.

In the illustrated example of FIG. 13, joint R1 is provided at a coordinate position of (0,0,0). The lengths between the joints R1 to R9 correspond to a length of the links. In the illustrated example, the end-effector 1202 is connected to the base 3404 via six joints, R1 to R6. The 3D space shown in FIG. 13 is modeled using a sequence of six homogeneous transformations, which may include matrix multiplications. The first six frames or joints R1 to R6 represent the forward kinematics of the robotic arm 210, and may be calculated using the Denavit-Hartenberg parameters of a robotic arm.

Joints R7 to R10 are part of the coupling plate 504. The rotation of the joints R7 to R10 is typically unknown to the robotic arm controller 4106 and is solved by the navigation computer system 302 as part of the End-Effector_T_Camera transformation. The three frames or joints R7 to R9 represent the transform from the tool-tip of the robotic arm 210 to a tip of the coupling plate 504. Frame or joint R7 represents the pitch joint of the coupling plate 504, which can change between 0° and 90°. Frame or joint R8 represents the yaw joint of the coupling plate 504, and can change between −90°, 0°, and 90°, depending on the yaw configuration. The last frame R10 represents the transform from the tool-tip of the coupling plate 504 to the control point of the stereoscopic camera 130.

The example navigation computer system 302 creates one or more 4×4 matrices that are representative or characteristic of the different pose differences between the base 3404 and the end-effector 1202 of the robotic arm 210. The navigation computer system 302 may create the matrix (matrices) by moving the robotic arm 210 to at least ten different poses to determine the relative transformations. The created 4×4 matrix comprises the End-Effector_T_Camera transformation.

Returning to FIG. 11, the example procedure 1100 continues by the navigation computer system 302 determining the Robot Base_T_Target transformation (block 1110). In this illustrated example, the Robot Base_T_Target transformation is known. For example, FIG. 12 shows the Robot Base_T_Target transformation as having a length of 1000 millimeters, which represents the distance between the base 3404 to the target surgical site 802. In some embodiments, this distance is measured by an operator and input into the navigation computer system 302.

The navigation computer system 302 next determines the unknown End-Effector_T_Camera transformation (block 1112). The known transformations determined by the navigation computer system 302 in blocks 1106 to 1110 are provided in 4×4 matrices that describe 3-space with numerical values that relate orientation and position (e.g., pose) that relate a remote space to a local space. Each 4×4 matrix includes a 3×3 rotational sub-matrix that relates orientation of the remote space to the local space. The 3×3 sub-matrix includes an n-vector that projects an x-axis of the remote space to a coordinate system of the local space, an o-vector that projects a y-axis of the remote space to the coordinate system of the local space, and an a-vector a projects a z-axis of the remote space to the coordinate system of the local space. In addition to the 3×3 sub-matrix, the 4×4 matrix includes a 3×1 D-vector that represents a position of an origin of the remote space in the coordinates of the local space.

Together, the transformations shown in FIG. 12 comprise a known chain of transformations. Accordingly, the navigation computer system 302 uses matrix multiplication to solve for the Effector_T_Camera transformation, as shown in Equation (1) below:

$$\text{End-Effector}\_T\_\text{Camera}=(\text{Robot Base}\_T\_\text{End-Effector})^{-1}*\text{Robot Base}\_T\_\text{Target}*\text{Target}\_T\_\text{Camera} \quad \text{(Equation 1)}$$

In Equation (1), (Robot Base_T_End-Effector)$^{-1}$ is the inverse matrix of matrix Robot Base_T_End-Effector such that the two matrices multiplied together produce the identity matrix. As shown in FIG. 12, the navigation computer system 302 is configured to solve for End-Effector_T_Camera A at one or more poses about the workspace.

It should be noted that due to mechanical tolerance, sag, movement of parts internal to the stereoscopic camera 130, etc., the End-Effector_T_Camera transformation varies with pose. However, by recording the actual End-Effector_T_Camera as a function of camera pose relative to the scene (e.g. the patient anatomy), the navigation computer system 302 removes the effects of each of these error contributions. These results hold their validity when the robotic arm 210 and the stereoscopic camera 130 are moved as a unit to a final production cart.

As shown in the example of FIG. 12, the end-effector 1202 is rotated 45 degrees about the x-axis of the base 3404, rotated 25 degrees about the y-axis of the base 3404, and is moved 900 mm away from the base 3404. These two transformations are represented as Robot Base_T_Target and Robot Base_T_End-Effector, respectively. Via the OpenCV calibrateCamera function, navigation computer system 302 determines that the stereoscopic camera 130 is a certain, more complex transformation away from the target as Target_T_Camera. The transformation from the camera to the robot end-effector 1202, End-Effector_T_Camera, is calculated using Equation (1), above. Robot Base_T_Target is a transformation of 1000 mm along the Z-axis. Also shown, "rot45X" is a rotation matrix that is 45 degrees about the X-axis. The navigation computer system 302 uses the known transformations to solve for the End-Effector_T_Camera transformation, as shown below.

using images recorded by the stereoscopic camera 130, and a pose of the robotic arm 210 and coupling plate 504. As such, when movement commands are received by the navigation computer system 302 from an operator, the navigation computer system 302 translates the movement commands into joint angle positions to cause the robotic arm 210 to move the stereoscopic camera 130 as intended by the operator. For instance, a simple "move Right" command may be translated by the navigation computer system 302 into complex joint movements for each of joints R1 to R6 of the robotic arm 210 to cause the camera 130 to move to the right, as intended.

In some embodiments, the navigation computer system 302 may also determine a transformation between the robotic space and the patient space (block 1114). The transformation between the robotic space and the patient space enables patient data, such as pre-operative images, models, or surgical navigation guides to be overlaid on the live stereoscopic video in real time in the correct orientation. In some embodiments this orientation is fixed. In other embodiments the orientation, if varying, is sensed and known. In some embodiments a patient is placed in an operating room bed and registered to the bed using one or more fiducials on the tracker 120. For example, if a patient is undergoing brain surgery, they are secured to a bed and an external frame is fixed to their skull. The frame is observable by the stereoscopic camera 130 and may comprise fiducials in an arrangement such as that of the calibration target where two or more non-collinear objects of known locations are visible simultaneously, such that the position and orientation of the frame, and hence the patient's skull, is capable of being determined. Other embodiments may use fiducials that are implanted into a patient and are visible in MM or similar images. Such fiducials on, for example, a tracker 120, can be used to accurately track and register a patient's skull as well as the MM image to a coordinate system representative of patient space. Further, other embodiments may use image recognition of features native to the patient themselves. For

| | | | | | |
|---|---|---|---|---|---|
| Robot Base_T_Target | row 0 | 1.0000 | 0.0000 | 0.0000 | 0.0000 |
| Robot Base_T_Target | row 1 | 0.0000 | 1.0000 | 0.0000 | 0.0000 |
| Robot Base_T_Target | row 2 | 0.0000 | 0.0000 | 1.0000 | 1000.0000 |
| Robot Base_T_Target | row 3 | 0.0000 | 0.0000 | 0.0000 | 1.0000 |
| rot45X | row 0 | 1.0000 | 0.0000 | 0.0000 | 0.0000 |
| rot45X | row 1 | 0.0000 | 0.7071 | −0.7071 | 0.0000 |
| rot45X | row 2 | 0.0000 | 0.7071 | 0.7071 | 0.0000 |
| rot45X | row 3 | 0.0000 | 0.0000 | 0.0000 | 1.0000 |
| Robot Base_T_End-Effector | row 0 | 0.9063 | 0.2988 | 0.2988 | 0.0000 |
| Robot Base_T_End-Effector | row 1 | 0.0000 | 0.7071 | −0.7071 | 0.0000 |
| Robot Base_T_End-Effector | row 2 | −0.4226 | 0.6409 | 0.6409 | 900.0000 |
| Robot Base_T_End-Effector | row 3 | 0.0000 | 0.0000 | 0.0000 | 1.0000 |
| Target_T_Camera | row 0 | 0.8859 | 0.4146 | 0.2081 | 93.1673 |
| Target_T_Camera | row 1 | −0.1475 | 0.6771 | −0.7210 | −208.4551 |
| Target_T_Camera | row 2 | −0.4398 | 0.6080 | 0.6610 | 102.1642 |
| Target_T_Camera | row 3 | 0.0000 | 0.0000 | 0.0000 | 1.0000 |
| Defined End-Effector_T_Camera | row 0 | 0.9888 | 0.1188 | −0.0907 | −1.0000 |
| Defined End-Effector_T_Camera | row 1 | −0.1214 | 0.9923 | −0.0240 | 10.0000 |
| Defined End-Effector_T_Camera | row 2 | 0.0872 | 0.0348 | 0.9956 | 304.8000 |
| Defined End-Effector_T_Camera | row 3 | 0.0000 | 0.0000 | 0.0000 | 1.0000 |
| Solved End-Effector_T_Camera | row 0 | 0.9888 | 0.1188 | −0.0907 | −1.0000 |
| Solved End-Effector_T_Camera | row 1 | −0.1214 | 0.9923 | −0.0240 | 9.9999 |
| Solved End-Effector_T_Camera | row 2 | 0.0872 | 0.0348 | 0.9956 | 304.8000 |
| Solved End-Effector_T_Camera | row 3 | 0.0000 | 0.0000 | 0.0000 | 1.0000 |

As discussed above, the End-Effector_T_Camera transformation is indicative of the position and orientation of the view vector of the stereoscopic camera 130. At this point, the navigation computer system 302 has a known correspondence between the view vector, as viewed by an operator example, facial or similar recognition using biometric data, in-situ x-ray, or similar alternative modality imaging can be used to precisely locate a position and orientation of the patient. In another example, a model of a surface of a patient's face can be determined using one or more depth map calculations as described above, and surface matching functions performed by the navigation computer system 302.

In an embodiment, a position and orientation of an operating room bed with respect to robot space is fixed and determined. Some embodiments comprise a rigid frame, which mechanically registers the bed to, for example, fittings on the cart 510 in a known position and orientation. Alternatively, the bed can be fixed with respect to the robotic arm 210 and fiducials can be used to determine position and orientation. For example, the robotic cart 510 and bed can be anchored to the floor and fixed for the duration of the procedure.

After visualization of the patient's fiducials by the stereoscopic camera 130, their position and orientation in robot space can be deciphered and stored by the navigation computer system 302, where coordinate system transformations from robot space to patient space are enabled. The robot space may correspond to the position of the base 3404, the end-effector 1202, and/or a pose of the robotic arm 210. It is noted that coordinate system transformations from one space to another are generally selectable and reversible. For example, it may be more efficient to transform desired camera motions or poses into robot space to enable the navigation computer system 302 to determine discrete joint motion and orientation. Alternatively, it may be easier and more efficient to present information to a surgeon on the display monitor 190 in patient space. Location of points and vectors can be transformed by the navigation computer system 302 to be respective of most any coordinate system, for example, a cart origin, a patient reference frame, GPS, and/or other coordinate systems as desired.

As shown in FIG. 11, after the transformations are determined for one or more poses, the navigation computer system 302 stores the matrices in a memory device (block 1116). The navigation computer system 302 uses the transformations to command movement of the robotic arm 210 using operator inputs provided in relation to a view vector of the stereoscopic camera 130. Further, the navigation computer system 302 may use patient space transformations to orient, overlay, or otherwise display patient data in conjunction with the live stereoscopic images. As the stereoscopic camera 130 is moved, the navigation computer system 302 also ensures the patient data orientation is changed to match the current view of the stereoscopic camera 130 using the patient space transformation. The example procedure 1100 of FIG. 11 continues until the surgical procedure ends.

In an example, an operator may actuate a control interface, such as a control pad, joystick, foot pedal, or a touch screen, to specify that a current view of the stereoscopic camera 130 is to move right and upwards from a current view. The operator's inputs are provided in relation to a current view vector of the stereoscopic camera 130, as displayed on a display monitor 190. The navigation computer system 302 receives a message or signal that is indicative of the control input. The navigation computer system 302 uses a correlation between the view vector of the stereoscopic camera 130 and the pose of the robotic arm 210 to translate the control input into pose movement data. As described above, this correlation is determined from the four transformations including the Robot Base_T_Target transformation, the Robot Base_T_End-Effector transformation, the End-Effector_T_Camera transformation, and the Target_T_Camera transformation.

As shown in FIG. 13, with the correlation, the navigation computer system 302 additionally knows the positions of joints R7 to R10 (or at least the positions and orientations of joints R7 and R10), including the view vector to the target surgical site. The pose movement data for the view vector, as expressed in coordinates in the robotic arm space, represents a delta from the current position of the robotic arm 210. In this example, the navigation computer system 302 determines how much the view vector, as shown as a dash lined line originating from point '10' of joint R10 and pointed downward through joint R9 in FIG. 13, is to move to match the control input provided by the operator. The navigation computer system 302 determines, for example, coordinates for the new view vector (e.g., new coordinates along the x, y, and z-axes) based on this delta corresponding to the pose movement data. The navigation computer system 302 then determines which of joints R1 to R6 of the robotic arm 210 are to be rotated, and an amount of rotation, to enable the view vector to reach the determined new coordinates. The navigation computer system 302 may use one or more robotic arm optimization algorithms to determine which joints are to be rotated. The navigation computer system 302 then determines one or more command messages or signals, which are transmitted to the robotic arm controller 4106, for causing the robotic arm 210 to move to the specified location.

In another example, to provide registration or alignment between live stereoscopic images and patient data, the navigation computer system 302 may accesses the camera parameters from one or more memories. The navigation computer system 302 also accesses, from the device 4104 of FIG. 10, an alternative modality of the image data (e.g., patient data), such as pre-surgical images, MM images, a 3D model of the surgical site from MRI or CT data, X-ray images, and/or surgical guides/templates. The navigation computer system 302 is configured to render a synthesized stereoscopic image of the alternative modality data using the camera parameters. The example navigation computer system 302 is also configured to provide the synthesized stereoscopic image for display via the display monitor 190. In some examples, the navigation computer system 302 is configured to fuse the synthesized stereoscopic image with the current stereoscopic visualization, where desirable aspects of each modality are visible and/or overlaid in identical perspective as if acquired by a single visualization device.

In some embodiments, the camera parameters are used by the navigation computer system 302 to match a synthesized stereoscopic image of alternative modality, for example MRI image data, to the stereoscopic perspective of the stereoscopic camera 130. Thus, the example navigation computer system 302 uses the stored calibration parameters (determined for the Target_T_Camera transformation) for stereoscopic image synthesis. In an example, the navigation computer system 302 uses the calibration parameters to fuse live stereoscopic images with a 3D model of a brain tumor that was imaged pre-operatively using an MM device. The example navigation computer system 302 uses the optical calibration parameters to select the corresponding location, size, and or orientation of the 3D model of the brain tumor that matches the stereoscopic images. In other words, the navigation computer system 302 selects a portion of the 3D model that corresponds to the view recorded by the stereoscopic camera 130. The navigation computer system 302 may also change which portion of the model is displayed based on detecting how the working distance, magnification, and/or orientation of the stereoscopic camera 130 changes, or based on how a pose of the robotic arm 210 changes.

The navigation computer system 302 may cause a graphical representation of the model to be overlaid of the stereoscopic images and/or cause the graphical representation of the model to appear visually fused with the stereoscopic images. The image processing performed by the navigation computer system 302 may include smoothing boundaries between the graphical representation of the model and the live stereoscopic view. The image processing may also include causing at least a portion of the graphical representation of the model to have an increased transparency to enable the underlying live stereoscopic view to also be visible to an operator.

In some examples, the navigation computer system 302 is configured to generate and/or render a depth map for every pixel in a stereoscopic image. The navigation computer system 302 may use the calibration parameters to determine, for example, tissue depth in an image. The navigation computer system 302 may use the depth information for image recognition to note tissue of interest and/or identify instrument location to avoid inadvertent contact when the stereoscopic camera 130 is mated with the robotic arm 210. The depth information may be output by the navigation computer system 302 to, for example, robotic suturing devices, diagnostic equipment, procedure monitoring and recording systems, etc., to conduct a coordinated and at least semi-automated surgical procedure.

FIG. 14 illustrates an example procedure 1400 or routine for calibrating the stereoscopic navigation system 300 when the Robot Base_T_Target transformation is unknown, according to an example embodiment of the present disclosure. Although the procedure 1400 is described with reference to the flow diagram illustrated in FIG. 14, it should be appreciated that many other methods of performing the steps associated with the procedure 1400 may be used. For example, the order of many of the blocks may be changed, certain blocks may be combined with other blocks, and many of the blocks described are optional. Further, the actions described in procedure 1400 may be performed among multiple devices including, for example the navigation computer system 302, the robotic arm 210, and/or the stereoscopic camera 130. For example, the procedure 1400 may be performed by a program stored in the memory device that is communicatively coupled to or part of the navigation computer system 302.

Blocks 1402 to 1408 are similar to the blocks 1102 to 1108 of FIG. 11. A description of blocks 1402 to 1408 is not repeated for brevity. At blocks 1410 and 1412, the navigation computer system 302 uses the known Target_T_Camera transformation and the Robot Base_T_End-Effector transformation to determine the unknown Robot Base_T_Target transformation and the End-Effector_T_Camera transformation.

In this embodiment, patient anatomy is used in place of a calibration object, which produces an unknown distance between the base 3404 and the target surgical site. The example navigation computer system 302 uses images of the patient anatomy recorded at different poses, as recorded by the left and right image sensors of the stereoscopic camera 130, to extract one or more patient features. The navigation computer system 302 matches the features across images, thereby enabling the extraction of the pose of the stereoscopic camera 130 relative to the patient features (equivalent to Target_T_Camera). Since the navigation computer system 302 has no knowledge of relative positions, orientations, and dimensions of the patient features, without further information, the navigation computer system 302 can at best only determine such poses up to a scale factor. However, a further calibration step, such as OpenCV's calibrateStereoCamera, is performed by the navigation computer system 302 to enable a determination of scale from the recorded stereoscopic images. From this calibration step, the navigation computer system 302 determines Target_T_Camera with the use of objects with unknown features (such as patient anatomy) to be used in an analytical method of determining the End-Effector_T_Camera transformation.

In this example, the Robot Base_T_Target transformation uses the patient anatomy as the target surgical site. The navigation computer system 302 is configured to set, calculate, and record, as appropriate, the known transformation information from many poses and use a set of multiple equations to estimate the unknown transformations as follows. For instance, the navigation computer system 302 adds an index i to Equation (1) to produce Equation (2), shown below.

$$\text{End-Effector\_}T\text{\_Camera}[i]=(\text{Robot Base\_}T\text{\_End-Effector})^{-1}*\text{Robot Base\_}T\text{\_Target}[i]*\text{Target\_}T\text{\_Camera} \quad \text{(Equation 2)}$$

Equation 2 is of the form: $Yi=A*Xi*B$. The index i progresses, for example, from 1 to the number of poses. This form is taken either as is or reworked such that the navigation computer system 302 determines solutions that minimize error. The navigation computer system 302 may also apply an optimizer method, such as Powell's method, to find a local minimum of a function to find solutions to the unknown Robot Base_T_Target transformation and the End-Effector_T_Camera transformation. By solving for these unknowns and keeping the robot arm 210 positioned rigidly to a patient reference frame so as not to move relative to the frame, the position and orientation of the camera view vector in the patient space is determinable as a function of the position of the robotic arm 210 for the duration of the analysis.

The example below illustrates an example in which the navigation computer system 302 determines solutions to the unknown Robot Base_T_Target transformation and the End-Effector_T_Camera transformation based on i=20 poses.

Solving $Y\_i=A*X\_i*B$

| True A Matrix: | | | |
|---|---|---|---|
| −0.61 | −0.23 | −0.76 | 2.76 |
| 0.49 | −0.87 | −0.13 | 0.15 |
| −0.63 | −0.44 | 0.64 | 7.61 |
| 0.00 | 0.00 | 0.00 | 1.00 |

| True B Matrix: | | | |
|---|---|---|---|
| 0.68 | −0.38 | −0.62 | 0.35 |
| 0.20 | 0.92 | −0.34 | −4.02 |
| 0.70 | 0.11 | 0.70 | 4.49 |
| 0.00 | 0.00 | 0.00 | 1.00 |

Estimated Solution

| A_est: | | | |
|---|---|---|---|
| −0.61 | −0.23 | −0.76 | 2.76 |
| 0.49 | −0.87 | −0.13 | 0.15 |
| −0.63 | −0.44 | 0.64 | 7.61 |
| 0.00 | 0.00 | 0.00 | 1.00 |

| B_est: | | | |
| --- | --- | --- | --- |
| 0.68 | −0.38 | −0.62 | 0.35 |
| 0.20 | 0.92 | −0.34 | −4.02 |
| 0.70 | 0.11 | 0.70 | 4.49 |
| 0.00 | 0.00 | 0.00 | 1.00 |

Data

| i = 0 X_i: | | | |
| --- | --- | --- | --- |
| 0.86 | −0.38 | 0.34 | 3.39 |
| 0.05 | −0.61 | −0.79 | −0.62 |
| 0.51 | 0.70 | −0.51 | 1.17 |
| 0.00 | 0.00 | 0.00 | 1.00 |
| Y_i (=A*X_i*B): | | | |
| −0.41 | 0.25 | 0.88 | 1.84 |
| 0.91 | 0.21 | 0.36 | 5.38 |
| −0.10 | 0.95 | −0.31 | 1.76 |
| 0.00 | 0.00 | 0.00 | 1.00 |
| i = 1 X_i: | | | |
| 0.82 | −0.50 | 0.27 | 2.95 |
| 0.01 | −0.46 | −0.89 | −1.23 |
| 0.57 | 0.73 | −0.38 | 0.55 |
| 0.00 | 0.00 | 0.00 | 1.00 |
| Y_i (=A*X_i*B): | | | |
| −0.44 | 0.26 | 0.86 | 2.51 |
| 0.89 | 0.04 | 0.45 | 6.68 |
| 0.08 | 0.96 | −0.25 | 2.56 |
| 0.00 | 0.00 | 0.00 | 1.00 |
| i = 2 X_i: | | | |
| 0.89 | −0.40 | 0.20 | 2.62 |
| 0.05 | −0.36 | −0.93 | −1.35 |
| 0.44 | 0.84 | −0.30 | 1.19 |
| 0.00 | 0.00 | 0.00 | 1.00 |
| Y_i (=A*X_i*B): | | | |
| −0.44 | 0.09 | 0.89 | 2.96 |
| 0.89 | −0.02 | 0.45 | 6.74 |
| 0.05 | 1.00 | −0.07 | 3.83 |
| 0.00 | 0.00 | 0.00 | 1.00 |
| i = 3 X_i: | | | |
| 0.90 | −0.33 | 0.29 | 2.85 |
| −0.02 | −0.69 | −0.72 | −0.98 |
| 0.44 | 0.64 | −0.63 | 0.85 |
| 0.00 | 0.00 | 0.00 | 1.00 |
| Y_i (=A*X_i*B): | | | |
| −0.30 | 0.27 | 0.92 | 2.86 |
| 0.94 | 0.27 | 0.22 | 4.77 |
| −0.18 | 0.92 | −0.33 | 1.79 |
| 0.00 | 0.00 | 0.00 | 1.00 |
| i = 4 X_i: | | | |
| 0.88 | −0.42 | 0.22 | 2.98 |
| 0.05 | −0.38 | −0.92 | −0.99 |
| 0.47 | 0.82 | −0.32 | 1.11 |
| 0.00 | 0.00 | 0.00 | 1.00 |
| Y_i (=A*X_i*B): | | | |
| −0.45 | 0.12 | 0.89 | 2.58 |
| 0.89 | −0.00 | 0.45 | 6.58 |
| 0.06 | 0.99 | −0.11 | 3.26 |
| 0.00 | 0.00 | 0.00 | 1.00 |

-continued

| i = 5 X_i: | | | |
| --- | --- | --- | --- |
| 0.82 | −0.48 | 0.30 | 3.22 |
| −0.00 | −0.54 | −0.84 | −0.66 |
| 0.57 | 0.70 | −0.44 | 1.01 |
| 0.00 | 0.00 | 0.00 | 1.00 |
| Y_i (=A*X_i*B): | | | |
| −0.42 | 0.29 | 0.86 | 1.85 |
| 0.91 | 0.11 | 0.40 | 5.89 |
| 0.02 | 0.95 | −0.31 | 2.10 |
| 0.00 | 0.00 | 0.00 | 1.00 |
| i = 6 X_i: | | | |
| 0.88 | −0.42 | 0.23 | 2.90 |
| −0.01 | −0.51 | −0.86 | −1.22 |
| 0.48 | 0.76 | −0.45 | 0.89 |
| 0.00 | 0.00 | 0.00 | 1.00 |
| Y_i (=A*X_i*B): | | | |
| −0.37 | 0.20 | 0.91 | 2.89 |
| 0.93 | 0.08 | 0.36 | 6.18 |
| −0.00 | 0.98 | −0.21 | 2.71 |
| 0.00 | 0.00 | 0.00 | 1.00 |
| i = 7 X_i: | | | |
| 0.87 | −0.47 | 0.16 | 2.62 |
| 0.02 | −0.29 | −0.96 | −1.03 |
| 0.49 | 0.84 | −0.25 | 0.52 |
| 0.00 | 0.00 | 0.00 | 1.00 |
| Y_i (=A*X_i*B): | | | |
| −0.46 | 0.12 | 0.88 | 3.23 |
| 0.88 | −0.11 | 0.47 | 6.88 |
| 0.15 | 0.99 | −0.06 | 3.59 |
| 0.00 | 0.00 | 0.00 | 1.00 |
| i = 8 X_i: | | | |
| 0.89 | −0.30 | 0.35 | 2.96 |
| 0.05 | −0.69 | −0.72 | −0.80 |
| 0.46 | 0.66 | −0.60 | 0.56 |
| 0.00 | 0.00 | 0.00 | 1.00 |
| Y_i (=A*X_i*B): | | | |
| −0.36 | 0.24 | 0.90 | 2.86 |
| 0.91 | 0.30 | 0.28 | 4.75 |
| −0.21 | 0.92 | −0.33 | 1.44 |
| 0.00 | 0.00 | 0.00 | 1.00 |
| i = 9 X_i: | | | |
| 0.87 | −0.34 | 0.36 | 3.22 |
| 0.05 | −0.67 | −0.74 | −0.68 |
| 0.49 | 0.66 | −0.57 | 1.05 |
| 0.00 | 0.00 | 0.00 | 1.00 |
| Y_i (=A*X_i*B): | | | |
| −0.38 | 0.26 | 0.89 | 2.13 |
| 0.91 | 0.28 | 0.31 | 4.94 |
| −0.17 | 0.93 | −0.34 | 1.58 |
| 0.00 | 0.00 | 0.00 | 1.00 |
| i = 10 X_i: | | | |
| 0.84 | −0.39 | 0.39 | 2.67 |
| 0.04 | −0.66 | −0.75 | −1.33 |
| 0.55 | 0.64 | −0.54 | 1.24 |
| 0.00 | 0.00 | 0.00 | 1.00 |
| Y_i (=A*X_i*B): | | | |
| −0.41 | 0.31 | 0.86 | 2.11 |
| 0.90 | 0.26 | 0.34 | 5.36 |
| −0.12 | 0.92 | −0.38 | 2.29 |
| 0.00 | 0.00 | 0.00 | 1.00 |

-continued

| i = 11 X_i: | | | |
|---|---|---|---|
| 0.90 | −0.40 | 0.18 | 3.10 |
| 0.00 | −0.40 | −0.92 | −1.35 |
| 0.44 | 0.82 | −0.36 | 1.01 |
| 0.00 | 0.00 | 0.00 | 1.00 |

| Y_i (=A*X_i*B): | | | |
|---|---|---|---|
| −0.39 | 0.11 | 0.91 | 2.93 |
| 0.92 | −0.00 | 0.40 | 6.78 |
| 0.05 | 0.99 | −0.10 | 3.26 |
| 0.00 | 0.00 | 0.00 | 1.00 |

| i = 12 X_i: | | | |
|---|---|---|---|
| 0.87 | −0.38 | 0.30 | 2.70 |
| 0.04 | −0.55 | −0.83 | −1.18 |
| 0.49 | 0.74 | −0.47 | 1.19 |
| 0.00 | 0.00 | 0.00 | 1.00 |

| Y_i (=A*X_i*B): | | | |
|---|---|---|---|
| −0.41 | 0.20 | 0.89 | 2.58 |
| 0.91 | 0.16 | 0.38 | 5.80 |
| −0.06 | 0.97 | −0.25 | 2.73 |
| 0.00 | 0.00 | 0.00 | 1.00 |

| i = 13 X_i: | | | |
|---|---|---|---|
| 0.88 | −0.43 | 0.22 | 3.28 |
| 0.03 | −0.41 | −0.91 | −1.31 |
| 0.48 | 0.80 | −0.35 | 0.53 |
| 0.00 | 0.00 | 0.00 | 1.00 |

| Y_i (=A*X_i*B): | | | |
|---|---|---|---|
| −0.43 | 0.15 | 0.89 | 2.88 |
| 0.90 | 0.01 | 0.43 | 6.97 |
| 0.05 | 0.99 | −0.14 | 2.71 |
| 0.00 | 0.00 | 0.00 | 1.00 |

| i = 14 X_i: | | | |
|---|---|---|---|
| 0.88 | −0.38 | 0.30 | 2.64 |
| 0.04 | −0.56 | −0.83 | −1.27 |
| 0.48 | 0.74 | −0.47 | 0.80 |
| 0.00 | 0.00 | 0.00 | 1.00 |

| Y_i (=A*X_i*B): | | | |
|---|---|---|---|
| −0.40 | 0.20 | 0.89 | 2.97 |
| 0.91 | 0.16 | 0.38 | 5.87 |
| −0.07 | 0.97 | −0.25 | 2.55 |
| 0.00 | 0.00 | 0.00 | 1.00 |

| i = 15 X_i: | | | |
|---|---|---|---|
| 0.90 | −0.39 | 0.18 | 2.99 |
| 0.01 | −0.40 | −0.91 | −1.15 |
| 0.43 | 0.83 | −0.36 | 1.05 |
| 0.00 | 0.00 | 0.00 | 1.00 |

| Y_i (=A*X_i*B): | | | |
|---|---|---|---|
| −0.39 | 0.10 | 0.91 | 2.98 |
| 0.92 | 0.01 | 0.39 | 6.52 |
| 0.03 | 0.99 | −0.10 | 3.26 |
| 0.00 | 0.00 | 0.00 | 1.00 |

| i = 16 X_i: | | | |
|---|---|---|---|
| 0.82 | −0.49 | 0.29 | 2.78 |
| 0.05 | −0.45 | −0.89 | −1.46 |
| 0.57 | 0.75 | −0.35 | 1.14 |
| 0.00 | 0.00 | 0.00 | 1.00 |

| Y_i (=A*X_i*B): | | | |
|---|---|---|---|
| −0.47 | 0.24 | 0.85 | 2.19 |
| 0.88 | 0.04 | 0.47 | 6.79 |
| 0.08 | 0.97 | −0.23 | 3.20 |
| 0.00 | 0.00 | 0.00 | 1.00 |

-continued

| i = 17 X_i: | | | |
|---|---|---|---|
| 0.86 | −0.40 | 0.33 | 3.29 |
| 0.01 | −0.62 | −0.78 | −0.78 |
| 0.52 | 0.67 | −0.53 | 1.21 |
| 0.00 | 0.00 | 0.00 | 1.00 |

| Y_i (=A*X_i*B): | | | |
|---|---|---|---|
| −0.38 | 0.28 | 0.88 | 1.91 |
| 0.92 | 0.20 | 0.33 | 5.40 |
| −0.09 | 0.94 | −0.33 | 1.87 |
| 0.00 | 0.00 | 0.00 | 1.00 |

| i = 18 X_i: | | | |
|---|---|---|---|
| 0.86 | −0.43 | 0.28 | 2.85 |
| 0.03 | −0.49 | −0.87 | −1.15 |
| 0.51 | 0.75 | −0.41 | 0.70 |
| 0.00 | 0.00 | 0.00 | 1.00 |

| Y_i (=A*X_i*B): | | | |
|---|---|---|---|
| −0.42 | 0.21 | 0.88 | 2.74 |
| 0.91 | 0.09 | 0.42 | 6.28 |
| 0.01 | 0.97 | −0.23 | 2.56 |
| 0.00 | 0.00 | 0.00 | 1.00 |

| i = 19 X_i: | | | |
|---|---|---|---|
| 0.82 | −0.44 | 0.36 | 3.43 |
| −0.00 | −0.63 | −0.78 | −1.25 |
| 0.57 | 0.64 | −0.52 | 0.98 |
| 0.00 | 0.00 | 0.00 | 1.00 |

| Y_i (=A*X_i*B): | | | |
|---|---|---|---|
| −0.40 | 0.33 | 0.86 | 1.76 |
| 0.91 | 0.20 | 0.35 | 5.99 |
| −0.06 | 0.92 | −0.38 | 1.78 |
| 0.00 | 0.00 | 0.00 | 1.00 |

| A_est: | | | |
|---|---|---|---|
| −0.61 | −0.23 | −0.76 | 2.76 |
| 0.49 | −0.87 | −0.13 | 0.15 |
| −0.63 | −0.44 | 0.64 | 7.61 |
| 0.00 | 0.00 | 0.00 | 1.00 |

| B_est: | | | |
|---|---|---|---|
| 0.68 | −0.38 | −0.62 | 0.35 |
| 0.20 | 0.92 | −0.34 | −4.02 |
| 0.70 | 0.11 | 0.70 | 4.49 |
| 0.00 | 0.00 | 0.00 | 1.00 |

The navigation computer system 302 uses the determined Robot Base_T_Target transformation and the End-Effector_T_Camera transformation for the different poses for commanding the robotic arm 210 based on operation inputs provided in a visual axis of the stereoscopic camera 130. As shown in FIG. 14, after the transformations are determined for one or more poses (including the patient space transformation at block 1414 if appropriate), the navigation computer system 302 stores the matrix transformations in a memory device (block 1416). The navigation computer system 302 uses the transformations to command movement of the robotic arm 210 using operator inputs provided in relation to a view vector of the stereoscopic camera 130. Further, the navigation computer system 302 may use patient space transformations to orient, overlay, or otherwise display patient data in conjunction with the live stereoscopic images. As the stereoscopic camera 130 is moved, the navigation computer system 302 also ensures the patient data orientation is changed to match the current view of the stereoscopic camera 130 using the patient space transformation. The example procedure 1400 of FIG. 14 continues until the surgical procedure ends.

Registration Embodiment

Figure 15:
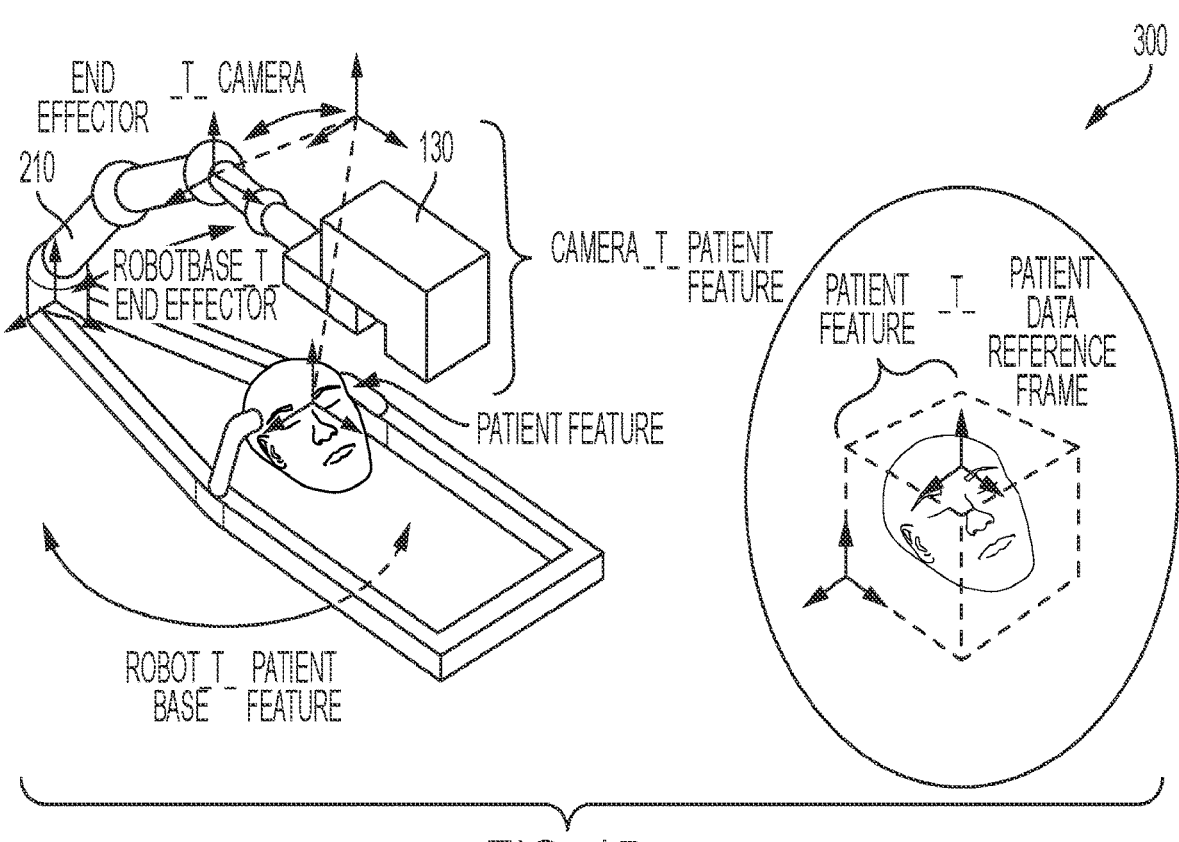
FIGS. 15 and 16 show diagrams of a Camera_T_Patient Feature transformation and a Patient Feature_T_Patient Data Reference Frame transformation, according to example embodiments or the present disclosure.
Figure 16:
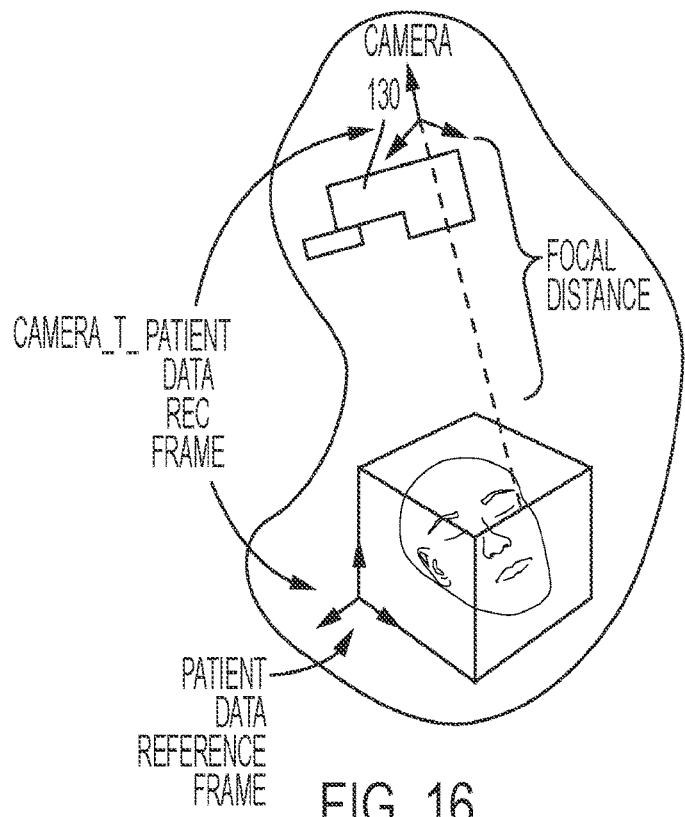

In some embodiments, the stereoscopic camera 130 is used by the navigation computer system 302 as a registration camera to determine the relative transformation between a patient frame and a camera frame. FIGS. 15 and 16 show diagrams of a Camera_T_Patient Feature transformation as well as a Patient Feature_T_Patient Data Reference Frame transformation, according to example embodiments or the present disclosure. The Camera_T_Patient Feature transformation and the Patient Feature_T_Patient Data Reference Frame are shown with respect to the other transformations described above.

The example navigation computer system 302 makes patient registration more accurate compared to traditional surgical navigation by using 3D surface extraction enabled by the stereoscopic camera 130 (as a dual-purpose camera). In other embodiments, the surface extraction is performed by the navigation computer system 302 using a dedicated depth-sensing camera (including but not limited to time-of-flight, IR laser projection and detection, structured light, etc.), which is registered in prior step(s) to the main stereoscopic camera 130.

In some instances, a region of a surface of the patient's anatomy much larger than available by a single pose of the surface extraction stereoscopic camera 130 is scanned by moving the robot-mounted stereoscopic camera 130 in a controlled manner about the patient. The resulting multiple images are merged by the navigation computer system 302 into one large detailed scan using 3D stitching techniques. Due to the same reason that tracking accuracy is significantly higher than the state of the art, the resolution of each piece of the scan (and of the final result) is significantly greater than the state of the art.

In each case of obtaining the extracted surface representation of the (external portion of the) live patient anatomy, the pose of one or more features of the surface is detected by the navigation computer system 302 relative to the camera as Camera_T_Patient Feature. The patient anatomy is considered rigid for this process. This extracted surface representation of the live patient anatomy is then matched by the navigation computer system 302 to the representation of the (external portion of the) patient anatomy represented in the patient data, such as CT or MM data. The matching is performed in a manner similar or identical to that used in surgical navigation. This results in the transformation Patient Feature_T_Patient Data Reference Frame. Equation (3) below shows the matrix relationship of the transformations.

> Camera Patient Data Reference
> Frame=Camera_*T*_End-Effector*End-Effector_
> *T*_Robot Base*Robot Base_*T*_Patient
> Feature*Patient Feature_*T*_Patient Data Refer-
> ence Frame                    (Equation 3)

As shown in FIGS. 15 and 16, this is the final transformation needed to enable determination of the pose of a camera view vector in the patient data space as a function of the pose of the robotic arm 210. In other words, the transformations shown in FIGS. 15 and 16 relate the patient data space to navigation of the robotic arm 210. This relation enables an operator to provide movement commands relative to the patient data space, such as via surgical navigation templates, pre-operative images, or 3D models. For example, an operator may move or rotate a surgical template. This input is translated by the surgical navigation computer system 302 using the transformations above into movement of the robotic arm 210 and/or the stereoscopic camera 130 to the specified new position of the template.

Further, this provides accurate registration of the live surgical view to the overlaid patient data, especially in instances where the patient data is orientated with respect to the robotic arm space or a default space corresponding to a base of the robotic arm 210 or other default location on the cart 510 or operative space.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A robotic surgical navigation system comprising:
   a robotic arm having a base section and an end-effector section;
   a stereoscopic camera connected to the end-effector section of the robotic arm; and
   a navigation computer system communicatively coupled to the robotic arm and the stereoscopic camera, the navigation computer system configured to:
      determine a first transformation between the stereoscopic camera and a target surgical site using at least one camera parameter,
      determine a second transformation between the end-effector section and the base section based on pose data from joint sensors within the robotic arm,
      determine a third transformation between the base section of the robotic arm and the target surgical site, wherein the third transformation includes a third transformation matrix that relates the orientation and position of the base section of the robotic arm and the position of the target surgical site, the third transformation matrix including a 4×4 matrix that relates the orientation and position of the base section of the robotic arm and a the position of the target surgical site,
      calculate a fourth transformation using the first transformation, the second transformation, and the third transformation, the fourth transformation representing a transformation between the end-effector section of the robotic arm and the stereoscopic camera,
      create a correlation between a view vector of the stereoscopic camera and a pose of the robotic arm using the first transformation, the second transformation, the third transformation, and the fourth transformation,
      receive an input command from an input device with respect to the view vector of the stereoscopic camera,
      determine at least one robotic arm command for the robotic arm using (i) the input command, and (ii) the correlation between the view vector of the stereoscopic camera and the pose of the robotic arm, and
      cause the robotic arm to move using the at least one robotic arm command.

2. The robotic surgical navigation system of claim 1, wherein the at least one camera parameter includes at least one of focal lengths at different magnifications, a working distance to the target surgical site, an interpupillary distance between image sensors of the stereoscopic camera, or a zoom repeat point, and wherein the at least one camera parameter includes information for modeling left and right image sensors of the stereoscopic camera as respective pinhole cameras.

3. The robotic surgical navigation system of claim 1, wherein the navigation computer system is configured to determine the at least one camera parameter using a calibration target having known features placed at the target surgical site during a calibration step.

4. The robotic surgical navigation system of claim 1, wherein the navigation computer system is configured to determine the first transformation for a plurality of poses for the stereoscopic camera, and determine the second transformation for a plurality of poses for the robotic arm.

5. The robotic surgical navigation system of claim 1, further comprising a coupling plate having a first side connected to the end-effector section of the robotic arm and a second end connected to the stereoscopic camera.

6. The robotic surgical navigation system of claim 1, wherein the first transformation includes a first transformation 4×4 matrix that relates a remote orientation and position of the target surgical site to a local space of the stereoscopic camera, the second transformation includes a second transformation 4×4 matrix that relates a remote orientation and position of the base section to a local space of the end-effector section of the robotic arm, and the fourth transformation includes a fourth transformation 4×4 matrix that relates a remote orientation and position of the end-effector section of the robotic arm to a local space of the stereoscopic camera.

7. The robotic surgical navigation system of claim 6, wherein each of the 4×4 transformation matrices includes a 3×3 rotational sub-matrix that relates the respective remote orientation to the respective local space and a 3×1 vector that specifies the respective remote position in a coordinate system of the respective local space, and wherein each 3×3 sub-matrix includes an n-vector that projects an x-axis of the respective remote orientation to the coordinate system of the respective local space, an o-vector that projects a y-axis of the respective remote orientation to the coordinate system of the respective local space, and an a-vector a projects a z-axis of the respective remote orientation to the coordinate system of the respective local space.

8. The robotic surgical navigation system of claim 1, wherein the navigation computer system is configured to determine the fourth transformation as a product of the first transformation, the third transformation, and an inverse of the second transformation.

9. The robotic surgical navigation system of claim 1, wherein the pose data includes information indicative of a rotation of each joint of the robotic arm and corresponds to a position and an orientation of the robotic arm.

10. The robotic surgical navigation system of claim 1, wherein the navigation computer system is configured to receive the second transformation as an input from an input device.

11. The robotic surgical navigation system of claim 1, wherein the navigation computer system is configured to:

determine a pose of one or more features of a target located at the target surgical site relative to the stereoscopic camera;

register one or more features of the target recorded in images recorded by the stereoscopic camera to corresponding features in a pre-operative image;

determine a transformation between the one or more features of the target to the pre-operative image; and determine a pose of the view vector of the stereoscopic camera in a target space as a function of the pose of the robotic arm using the transformation between the one or more features of the target to the pre-operative image and the determined correlation between the view vector of the stereoscopic camera and the pose of the robotic arm.

12. The robotic surgical navigation system of claim 1, wherein the input device includes at least one of a joystick, a control pad, a touchscreen, a foot pedal, or a force sensor connected to the stereoscopic camera.

13. A surgical navigation method comprising:

receiving, in a navigation computer system, a request message to calibrate a robotic arm having a base section and an end-effector section, the end-effector section connected to a stereoscopic camera via a coupling plate;

determining, via the navigation computer system, a first transformation between the stereoscopic camera and a target surgical site using at least one camera parameter;

determining, via the navigation computer system, a second transformation between the end-effector section and the base section of the robotic arm based on pose data from joint sensors within the robotic arm;

calculating, via the navigation computer system, a third transformation between a position and orientation of the base section of the robotic arm and the target surgical site and a fourth transformation between the end-effector section of the robotic arm and the stereoscopic camera using the first transformation and the second transformation for a plurality of poses;

creating, via the navigation computer system, a correlation between a view vector of the stereoscopic camera and a pose of the robotic arm using the first transformation, the second transformation, the third transformation, and the fourth transformation;

receiving, in the navigation computer system from an input interface, an input command entered by an operator with respect to the view vector of the stereoscopic camera;

determining, via the navigation computer system, at least one robotic arm command for the robotic arm using (i) the input command, and (ii) the correlation between the view vector of the stereoscopic camera and the pose of the robotic arm; and transmitting from the navigation computer system, the at least one robotic arm command to cause the robotic arm to move the stereoscopic camera according to the input command.

14. The surgical navigation method of claim 13, wherein calculating the third transformation and the fourth transformation includes solving for, via the navigation computer system, a local minimum of a function relating the first transformation, the second transformation, the third transformation, and the fourth transformation for the plurality of poses.

15. The surgical navigation method of claim 13, wherein the input command includes at least one of move right, move left, move up, move down, move diagonally, move closer to the target surgical site, move further away from the target surgical site, rotate along a yaw axis, rotate along a roll axis, rotate along a pitch axis, increase a zoom magnification of the stereoscopic camera, or decrease a zoom magnification of the stereoscopic camera.

16. The surgical navigation method of claim 13, wherein the at least one robotic arm command includes an amount of rotation for at least one joint of the robotic arm.

17. The surgical navigation method of claim 13, further comprising storing to a memory device, via the navigation computer system, the correlation between the view vector of the stereoscopic camera and the pose of the robotic arm.

18. The surgical navigation method of claim 13, further comprising storing to a memory device, via the navigation computer system, the first transformation, the second transformation, the third transformation, and the fourth transformation.

19. The surgical navigation method of claim 13, wherein determining the at least one robotic arm command includes:

translating, via the navigation computer system, the input command into a movement delta of the view vector expressed in a coordinate system of the robotic arm using the correlation between the view vector of the stereoscopic camera and the pose of the robotic arm;

determining, via the navigation computer system, new coordinates for the view vector in the coordinate system of the robotic arm using the movement delta;

determining joints of the robotic arm and an amount of rotation of the determined joints for moving the view vector to the new coordinates; and creating the at least one robotic arm command based on the determined joints and the determined amount of rotation for the determined joints.

20. The surgical navigation method of claim 19, wherein the correlation between the view vector of the stereoscopic camera and the pose of the robotic arm includes an expression of the view vector of the stereoscopic camera in a coordinate system of the robotic arm.

* * * * *